United States Patent [19]

Parish et al.

[11] Patent Number: 6,143,730

[45] Date of Patent: Nov. 7, 2000

[54] PREPARATION AND USE OF SULFATED OLIGOSACCHARIDES

[75] Inventors: Christopher Richard Parish, Campbell; William Butler Cowden, Kambah, both of Australia

[73] Assignee: The Australian National University, Acton, Australia

[21] Appl. No.: 08/945,937

[22] PCT Filed: Apr. 24, 1996

[86] PCT No.: PCT/AU96/00238

§ 371 Date: Oct. 28, 1997

§ 102(e) Date: Oct. 28, 1997

[87] PCT Pub. No.: WO96/33726

PCT Pub. Date: Oct. 31, 1996

[30] Foreign Application Priority Data

Apr. 28, 1995 [AU] Australia ................. PN 2618

[51] Int. Cl.[7] .................. A61K 31/715; A01N 43/04
[52] U.S. Cl. .................. 514/54; 514/2; 514/24; 514/25; 514/53; 514/61; 536/4.1; 536/59; 536/109; 536/118
[58] Field of Search ................... 514/53, 54, 56, 514/61, 23, 24, 25, 2; 536/4.1, 118, 59, 109

[56] References Cited

U.S. PATENT DOCUMENTS

| | | |
|---|---|---|
| 5,034,520 | 7/1991 | Lormeau et al. . |
| 5,447,919 | 9/1995 | Hosang et al. ............... 514/53 |
| 5,459,257 | 10/1995 | Shoji et al. ............... 536/118 |
| 5,506,210 | 4/1996 | Parish et al. ............... 514/23 |
| 5,541,166 | 7/1996 | Parish et al. ............... 514/56 |
| 5,739,115 | 4/1998 | Fugedi et al. ............... 514/24 |

FOREIGN PATENT DOCUMENTS

| | | |
|---|---|---|
| 0 338 092 A1 | 10/1988 | European Pat. Off. . |
| 0 504 645 A2 | 3/1992 | European Pat. Off. . |
| WO 95/09637 | 4/1995 | WIPO . |

*Primary Examiner*—James O. Wilson
*Attorney, Agent, or Firm*—Fulwider, Patton Lee & Utecht, LLP

[57] ABSTRACT

Sulfated oligosaccharides, wherein the oligosaccharide has the general formula I:

$$R_1 - (R_x)_n - R_2 \qquad (I)$$

wherein $R_1$ and $R_2$ and each $R_x$ represents a monosaccharide unit, all of which may be the same or different, adjacent monosaccharide units being linked by $1 \rightarrow 2$, $1 \rightarrow 3$, $1 \rightarrow 4$ and/or $1 \rightarrow 6$ glycosidic bonds and n is an integer of from 1 to 6, and use thereof as anti-angiogenic, anti-metastatic and/or anti-inflammatory agents.

25 Claims, 7 Drawing Sheets

ANGIOGENESIS CONTROL

20 μg/ml MALTOHEXAOSE SULPHATE

PREPARATION AND USE OF SULFATED OLIGOSACCHARIDES

FIELD OF THE INVENTION

This invention relates to sulfated oligosaccharides, their preparation and use as anti-angiogenic, anti-metastatic and/or anti-inflammatory agents.

BACKGROUND TO THE INVENTION

Heparan sulfates belong to the glycosaminoglycan family of polysaccharides. They are present in most multicellular animals and have a ubiquitous distribution, being expressed on the cell surface and in the extracellular matrices (ECM) of most tissues (1, 2). Heparan sulfates usually exist as proteoglycans and there has been considerable progress in sequencing and cloning the core polypeptides of the molecule. So far, for example, at least eight different heparan sulfate proteoglycan (HSPG) core polypeptides have been identified on the cell surface (3).

Initially HSPGs were considered to play largely a structural role on the cell surface and in the ECM. However, heparan sulfate chains exhibit remarkable structural diversity (2, 4) which suggests that they may provide important signalling information for many biological processes. Thus, although heparan sulfate chains are initially synthesised as a simple alternating repeat of glucuronosyl and N-acetylglucosaminyl residues joined by β1–4 and α1–4 linkages there are many subsequent modifications. The polysaccharide is N-deacetylated and N-sulfated and subsequently undergoes C5 epimerisation of glucuronosyl units to iduronosyl units, and various O-sulfations of the uronosyl and glucosaminyl residues. The variability of these modifications allows for some thirty different disaccharide sequences which, when arranged in different orders along the heparan sulfate chain, can theoretically result in a huge number of different heparan sulfate structures. In this regard, the anticoagulant polysaccharide heparin, present only in mast cell granules, represents an extreme form of heparan sulfate where epimerisation and sulfation have been maximised. Most heparan sulfates contain short stretches of highly sulfated residues joined by relatively long stretches of non-sulfated units.

There is now clear evidence that heparan sulfates play a critical role in a wide range of biological processes (2–4). In particular, they can act as ligands for adhesion molecules involved in cell—cell interactions (5, 6), participate in cell-ECM interactions (5, 6) and act as essential cell surface receptors for growth factors such as basic fibroblast growth factor (bFGF) (7, 8) and vascular endothelial growth factor (VEGF) (9). HSPGs are also a key component of basement membranes, which represent a major barrier to cell migration (10). Basement membrane barriers can only be breached when cells deploy a range of degradative enzymes (11) including an endoglycosidase, termed heparanase, which cleaves heparan sulfate chains (12, 13).

It has been shown that many of the biological processes in which heparan sulfates participate involve the recognition of unique heparan sulfate structures, with the position of the sulfates in the polysaccharide chain being of critical importance (3). For example, it has been demonstrated that defined heparan sulfate sequences are recognised by acidic and basic FGF (14–16) and cleaved by heparanases. Based on these observations, it has been an objective of the present inventors to synthesise sulfated oligosaccharides which block heparan sulfate recognition by growth factors, and inhibit cleavage of heparan sulfates by heparanases. In the case of blocking of growth factors, it was considered that low molecular weight mimics of heparan sulfate should be particularly effective, as it is now believed that cell surface heparan sulfates mediate the cross linking of growth factors bound to their receptors (17). Furthermore, sulfated oligosaccharides should be effective heparanase inhibitors by acting as non-cleavable substrates of this enzyme.

Sulfated oligosaccharides with growth factor inhibitory activity have a number of clinical uses. Heparin/heparan sulfate binding growth factors, such as bFGF and VEGF, are potent inducers of angiogenesis (18). In adults, angiogenesis is a relatively rare occurrence except during wound healing. However, there are a number of "angiogenesis-dependent diseases" in adults where angiogenesis is critically important (18–20). The most important of these is the angiogenesis associated with the growth of solid tumours, proliferative retinopathies and rheumatoid arthritis. Sulfated oligosaccharides which blocked the action of key angiogenic growth factors, such as bFGF and VEGF, would be particularly useful for the treatment of these angiogenesis-dependent diseases.

Similarly, sulfated oligosaccharides which inhibit heparanase action have a number of clinical applications. The subendothelial basement membrane represents a major physical barrier for the passage of endothelial cells, tumour cells and leukocytes through the blood vessel wall. The heparanase enzyme, combined with a range of proteolytic enzymes (eg, plasmin, matrix metalloproteinases), plays an essential part in basement membrane degradation by invading cells (11–13, 21). Thus, by preventing basement membrane degradation, sulfated oligosaccharides with heparanase-inhibitory activity should exhibit anti-metastatic and anti-inflammatory activity, and in addition may inhibit early stages of angiogenesis. The use of sulfated oligosaccharides which simultaneously inhibit angiogenic growth factor action and the heparanase enzyme would be preferred in many clinical situations, eg, treatment of highly metastatic solid tumours and rheumatoid arthritis.

Prior International Patent Application No. PCT/AU88/00017 (Publication No. WO 88/05301) discloses the use of sulfated polysaccharides such as heparin and modified heparin, fucoidin, pentosan sulfate, dextran sulfate and carrageenin lambda, which block or inhibit heparanase activity, in anti-metastatic and/or anti-inflammatory treatment of an animal or human patient.

In work leading to the present invention, the inventors have prepared sulfated oligosaccharides using either naturally occurring oligosaccharides or totally synthetic oligosaccharides comprising hexose-containing homopolymers. Some of these compounds have been demonstrated to be potent inhibitors of human angiogenesis, tumor metastatis and inflammation. The data obtained is consistent with the sulfated oligosaccharides exhibiting their biological effects by inhibiting angiogenic growth factor action and/or heparanase function, and certain sulfated oligosaccharides have been obtained which are potent inhibitors of both angiogenesis and heparanase activity.

SUMMARY OF THE INVENTION

In accordance with one aspect, the present invention provides sulfated oligosaccharides, wherein the oligosaccharide has the general formula I:

$$R_1-(R_x)_n-R_2 \qquad (I)$$

wherein $R_1$ and $R_2$ and each $R_x$ represents a monosaccharide unit, all of which may be the same or different, adjacent monosaccharide units being linked by 1→2, 1→3, 1→4 and/or 1→6 glycosidic bonds; and n is an integer of from 1 to 6.

The sulfated oligosaccharides in accordance with this invention are based on polymers of monosaccharide units, which may be linked by 1→2, 1→3, 1→4 and/or 1→6 glycosidic bonds and which may consist of from 3 to 8 monosaccharide units. Preferably, the oligosaccharides consist of from 3 to 6 monosaccharide units (that is n is from 1 to 4), more preferably from 5 to 6 monosaccharide units (n is from 3 to 4). The polymers may comprise homopolymers containing only one type of monosaccharide unit, or heteropolymers containing two or more different types of monosaccharide units.

The monosaccharide units which are linked together to form the oligosaccharides are preferably hexoses, and may be either furanoses such as fructose or pyranoses such as glucose, mannose, altrose, allose, talose, galactose, idose, or gulose. The hexoses may be in either the D- or the L-configuration.

In one particular aspect of the present invention, there are provided novel, synthetic oligosaccharides having the general formula II:

$$R_y—(R_y)_n—R_y \qquad (II)$$

wherein each $R_y$ group is the same and each represents a monosaccharide unit, adjacent monosaccharide units being linked by 1→3, 1→4 and/or 1→6 glycosidic bonds; and n is an integer of from 1 to 6.

In this particular aspect, the invention also provides sulfated oligosaccharides, wherein the oligosaccharide has the general formula II above.

Preferably, in the homopolymeric oligosaccharides of formula II, the monosaccharide unit is a hexose such as glucose, mannose, altrose, allose, talose, galactose, idose or gulose. Preferably also, in these oligosaccharides n is from 1 to 4, more preferably from 3 to 4.

The oligosaccharides of general formulae I and II also include compounds wherein the monosaccharide units are derivatised, in particular where the units are phosphate, acetyl or other ester derivatives of monosaccharides.

In general, the sulfated oligosaccharides of this invention may be prepared by sulfation of the oligosaccharides by methods known per se in the art to give their corresponding O-sulfated derivatives. Suitable sulfation methods are exemplified below. The oligosaccharides to be sulfated may be naturally occurring products including oligosaccharides occurring naturally as such (for example raffinose and stachyose), as well as oligosaccharides prepared by enzymatic or chemical degradation of naturally occurring polysaccharides (for example maltotetraose, maltopentoase and maltohexaose; glucotriose, glucotetraose and glucopentaose; chondroitin tetra-, hexa- and octasaccharides; and mannopentaose phosphate from the yeast *Pichia holstii*).

As previously described, sulfated oligosaccharides falling within the scope of this invention have been shown to exhibit heparanase inhibitory and/or growth factor inhibitory activity, and accordingly in yet another aspect of the present invention extends to the use of a sulfated oligosaccharide as described above as an anti-angiogenic, anti-metastatic and/or anti-inflammatory agent in the treatment of a warm-blooded animal (including a human) patient.

Thus, the present invention extends to a method for the anti-angiogenic, anti-metastatic and/or anti-inflammatory treatment of a human or other warm-blooded animal patient in need of such treatment, which comprises administration to the patient of an effective amount of at least one sulfated oligosaccharide as described above.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

The invention also extends to the use in the manufacture of a medicament for the anti-angiogenic, anti-metastatic and/or anti-inflammatory treatment of a human or other warm-blooded animal patient of at least one sulfated oligosaccharide as described above.

Furthermore, this invention also provides a pharmaceutical or veterinary composition for anti-angiogenic, anti-metastatic and/or anti-inflammatory treatment, which comprises at least one sulfated oligosaccharide as described above, together with a pharmaceutically and veterinarily acceptable carrier or diluent therefor.

The formulation of such therapeutic compositions is well known to persons skilled in this field. Suitable pharmaceutically or veterinarily acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically and veterinarily active substances is well known in the art, and it is described, by way of example, in *Remington's Pharmaceutical Sciences,* 18th Edition, Mack Publishing Company, Pennsylvania, U.S.A. Except insofar as any conventional media or agent is incompatible with the active ingredient, use thereof in the pharmaceutical and veterinary compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human or animal subjects to be treated; each unit containing a predetermined quantity of active ingredient calculated to produce the desired therapeutic effect in association with the required pharmaceutical or veterinary carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

The sulfated oligosaccharides of this invention may be used in the treatment of angiogenesis-dependent diseases including angiogenesis associated with the growth of solid tumours, proliferative retinopathies and rheumatoid arthritis, as well as in the treatment of inflammatory diseases and conditions in which the heparanase-inhibitory activity of the sulfated oligosaccharides would be particularly useful in inhibiting leukocyte infiltration, including chronic inflammatory diseases where leukocyte infiltration is a key element such as rheumatoid arthritis, multiple sclerosis, insulin dependent diabetes mellitus, inflammatory bowel diseases such as ulcerative colitis and Chron's disease, allograft rejection and chronic asthma.

Throughout this specification, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

Figure 1A:
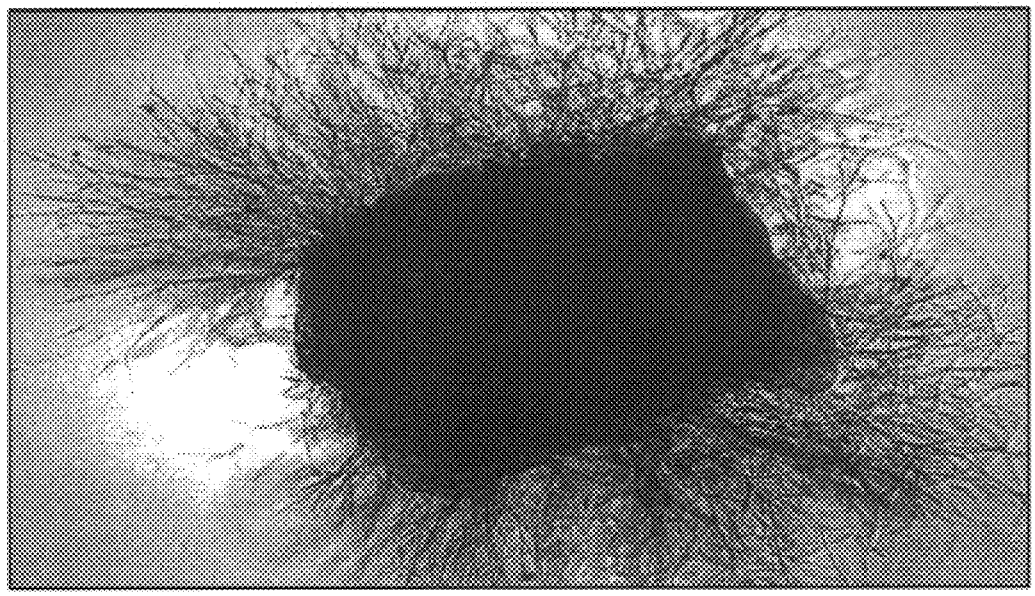

As broadly described above, the present invention relates to sulfated oligosaccharides and to their use as anti-angiogenic, anti-metastatic and/or anti-inflammatory agents.

Some oligosaccharides can be obtained from natural sources for subsequent sulfation, however, a simple procedure for synthesising oligosaccharides of defined chain length and stereochemistry is highly desirable. The present invention provides an improved method for synthesising and isolating oligomers of hexose sugars from simple starting materials in good yields wherein the sugar monomers of these oligomers are linked with a 1→3, 1→4 and/or 1→6 linkage. This method for manufacturing oligomers of hexose sugars contrasts sharply with the manner in which such sugar oligomers have previously been manufactured in that good yields are obtained, the degree of oligomerisation is readily controlled and the products derived from this method are homologous linear oligomers which are easily isolated and purified using simple chromatographic techniques.

Many examples which describe methods for preparing sugar polymers and oligomers can be found in the scientific and patent literature. For example, in a commonly used procedure an unmodified sugar monomer, either alone or in the presence of solvent, may be heated in the presence of a catalyst to give branched and linear polymeric products with various and sometimes ill-defined chemical linkages (22, 23). Another method where the sugar is melted in the presence of cation exchange resins (24) also gives high molecular weight highly branched polymers. In these two examples, the polymers are formed with the concomitant loss of one molecule of water for each polymer bond formed. Another example of a known method of step-wise polymerisation involves utilising the Koenigs-Knorr reaction where sugars possessing nonhydroxylic groups (such as a bromine or chlorine atom) in position-1 and protecting groups (such as acetyl) on other sugar hydroxyl groups are caused to react at position-1 with a hydroxyl group on another sugar (24). In these methods a molecule other than water, for example HBr, is lost during the polymer bond formation. This method of preparing oligosaccharides is tedious, requires the preparation of complex starting materials and gives poor overall yields (25).

In a similar manner it is known that a hexose sugar containing a primary alcohol group on carbon 6 and O-protecting groups (such as acetyl) at positions 2,3 and 4 and a leaving group such as bromine in position 1 will self-condense, especially in the presence of a catalyst such as silver oxide, to give 1,6 linked polymers; a series of gentiodextrins have been prepared in this manner from 1-bromo-2,3,4-tri-O-acetyl-α-D-glucose: however yields of the oligosaccharides were low due to the formation of 1,6-anhydro-β-D-glucose derived from intramolecular condensation; yields of the dimer (14%) and trimer (22%) were not good and yields of the tetramer and pentamer were worse ($\leq$5%) and the hexamer was isolated in only 1% yield (26).

More recent publications describe chemical syntheses of polymers of 1,6-linked-β-pyranosyl units (27) and D-dextran (28), made by the ring-opening polymerisation reaction of anhydrosugar derivatives. This method is hampered by the considerable effort needed to prepare the anhydrosugar starting material and there is no evidence that oligosaccharides can be readily prepared by this method even though the reactions are carried out at, for example, −60° C. Another method has employed acid catalysed melt polymerisation of 1,2,3,4-tetra-O-acetyl-β-D-glucose to prepare a mixture of 1,6'-linked oligosaccharide acetates which, upon deacetylation and subjection to chromatographic examination, was shown to contain mostly mono and disaccharides, namely glucose (15%), levoglucosan (4%) and gentiobiose (16%) while the oligosaccharide yield was unacceptably low, specifically, gentiotriose (4%) and gentiotetraose (0.6%) (29). This method was described subsequently in greater detail (30) and although the yield of polymerised products was improved upon slightly it resulted in only very poor yields of the expected oligomers.

It thus appears from the literature that, although several procedures already exist for preparing a number of oligosaccharides, no method for synthesising homo-oligosaccharides in good yield from readily available and inexpensive starting material has been described to date.

In work leading to this invention, the inventors have discovered a process whereby specific hexopyrano-oligosaccharides can be synthesised in good yields from readily available and inexpensive starting materials. In accordance with this aspect of the invention, there is provided a process for the preparation of hexopyrano-oligosaccharides which comprises heating an acetyl or other ester derivative of a hexose in an inert solvent under reduced pressure and in the presence of a Lewis acid or other catalyst.

In accordance with this process, the oligomerisation of derivatised hexose sugars, including but not restricted to 1,2,3,4-tetra-O-acetyl derivatives of glucose, mannose, galactose, altrose, talose, gulose, idose and allose can be made to take place in a controlled manner to give O-acetylated hexose oligosaccharides. In this process, the degree of oligomerisation (chain length) can readily be controlled by manipulation of the temperature at which the oligomerisation reaction takes place and by varying the time over which the reaction is allowed to proceed. Following the oligomerisation reaction, the crude product mixture may be subjected to further acetylation, in order to acetylate the remaining free hydroxyl groups of the oligosaccharides. The acetylated oligosaccharides can then be readily separated by adsorption chromatography. The acetyl groups have ultra-violet light absorbance, facilitating the use of spectrophotometry for identifying the acetylated oligosaccharides as they are sequentially eluted from the column. The acetyl protecting groups can also be removed from the oligosaccharide mixture, and the resulting oligosaccharides separated according to size by gel filtration (size exclusion) chromatography.

In the Examples described herein, the sulfated oligosaccharides are isolated and used as their respective sodium salts. It will be understood that other pharmaceutically acceptable salts, such as calcium or pharmaceutically acceptable amine salts, may be isolated and used in the corresponding manner. Accordingly, references herein to a "sulfated oligosaccharide" are to be understood as including such sodium or other pharmaceutically acceptable salts of the sulfated oligosaccharide.

Further features of the present invention are more fully described in the following Example(s). It is to be understood, however, that this detailed description is included solely for the purposes of exemplifying the present invention, and should not be understood in any way as a restriction on the broad description of the invention as set out above.

Examples 1, 2 and 3 exemplify the preparation of synthetic oligosaccharides by the novel process disclosed herein, Examples 4, 5 and 6 exemplify processes for the sulfation of oligosaccharides, and Example 7 exemplifies the use of sulfated oligosaccharides as anti-angiogenic, anti-metastatic and/or anti-inflammatory agents. (In Examples 1 and 2, "ND" represents "not determined".)

Figure 1B:
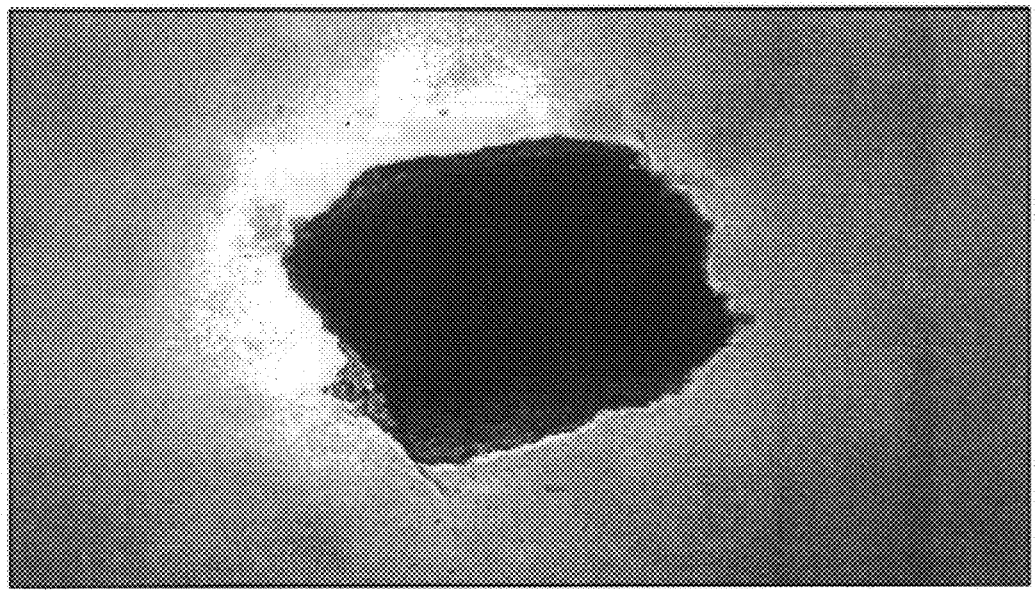

In the accompanying drawings:

FIGS. 1A and 1B show the effect of maltohexaose sulfate on human angiogenesis in vitro. FIG. 1A is a digital image of control angiogenesis 14 days following culture initiation. FIG. 1B depicts angiogenesis in the presence of 20 μg/ml of maltohexaose sulfate.

Figure 2:
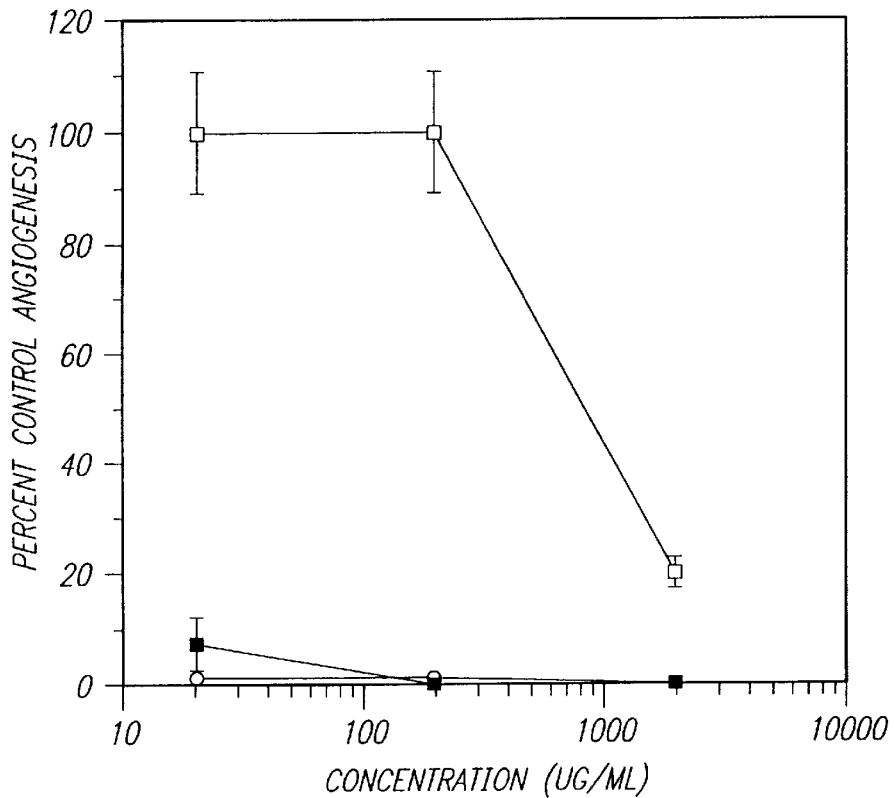

FIG. 2 shows the effect of different concentrations of maltose sulfate (□), maltotetraose sulfate (○) and maltohexaose sulfate (■) on human angiogenesis in vitro. Data obtained from digital images of angiogenic response 14 days following culture initiation. Each value mean±standard error (n=4).

Figure 3:
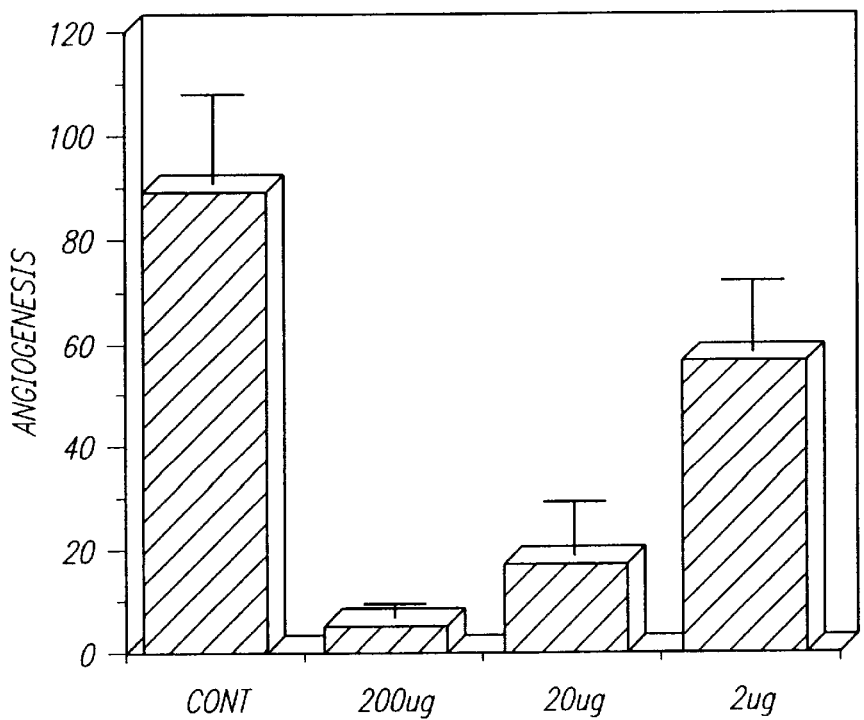

FIG. 3 shows the effect of different concentrations (μg/ml) of sulfated mannopentaose phosphate from *Pichia holstii* on human angiogenesis in vitro. Data obtained from digital images of angiogenic response 19 days following culture initiation. Each value mean±standard error (n=4).

Figure 4:
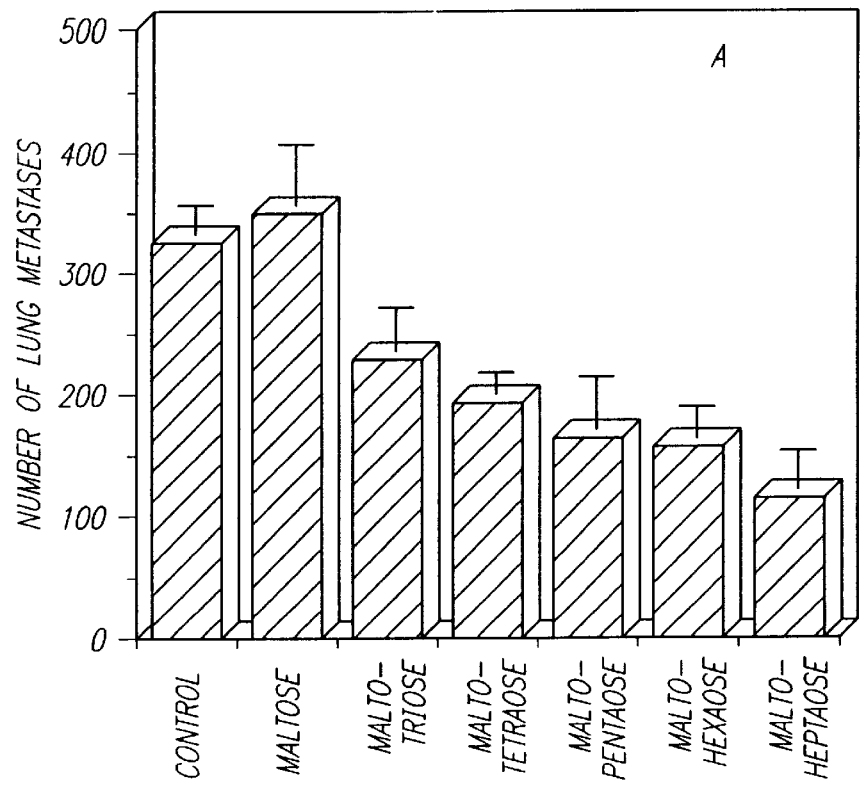
Figure 4:
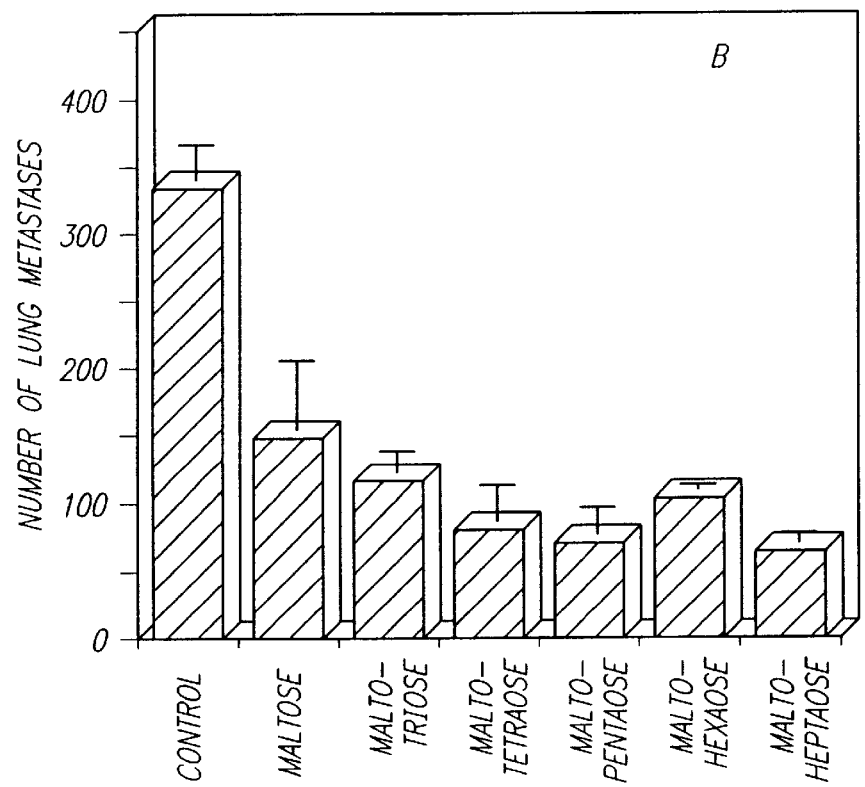

FIG. 4 shows the effect of sulfated maltose oligosaccharides of different chain length on the metastasis of the rat mammary adenocarcinoma 13762 MAT. Control animals received 13762 MAT cells in the absence of oligosaccharide. In panel A treated animals received 2 mg, i.v., of each compound at the time of tumour cell injection. In panel B treated animals received 4 mg, subcut., of each compound at the time of tumour cell injection. Vertical bars represent standard errors of means.

Figure 5:
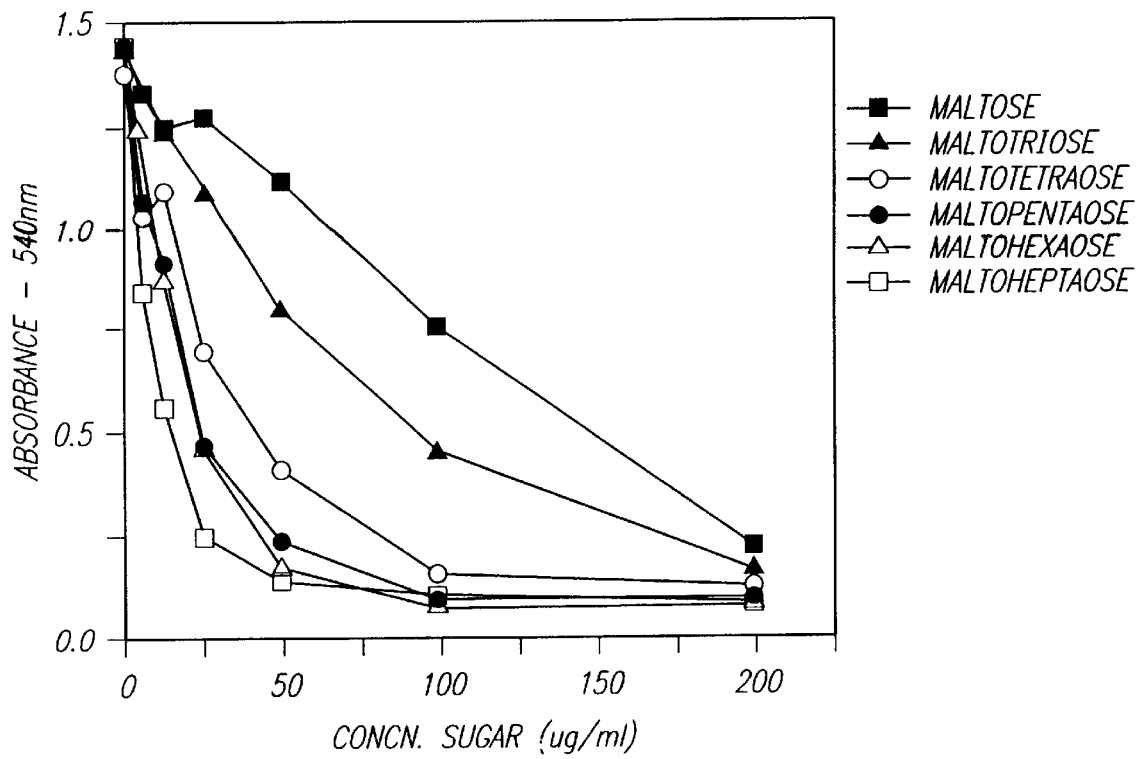

FIG. 5 is an assessment of the ability of sulfated maltose oligosaccharides of different chain length to inhibit the binding of cell surface heparan sulfates on BALB/c 3T3 cells to immobilised aFGF. Bound 3T3 cells were quantified by Rose Bengal staining and by measuring dye absorbance at 540 nm. The degree of sulfation of the different maltose oligosaccharides is listed in Table 2.

Figure 6:
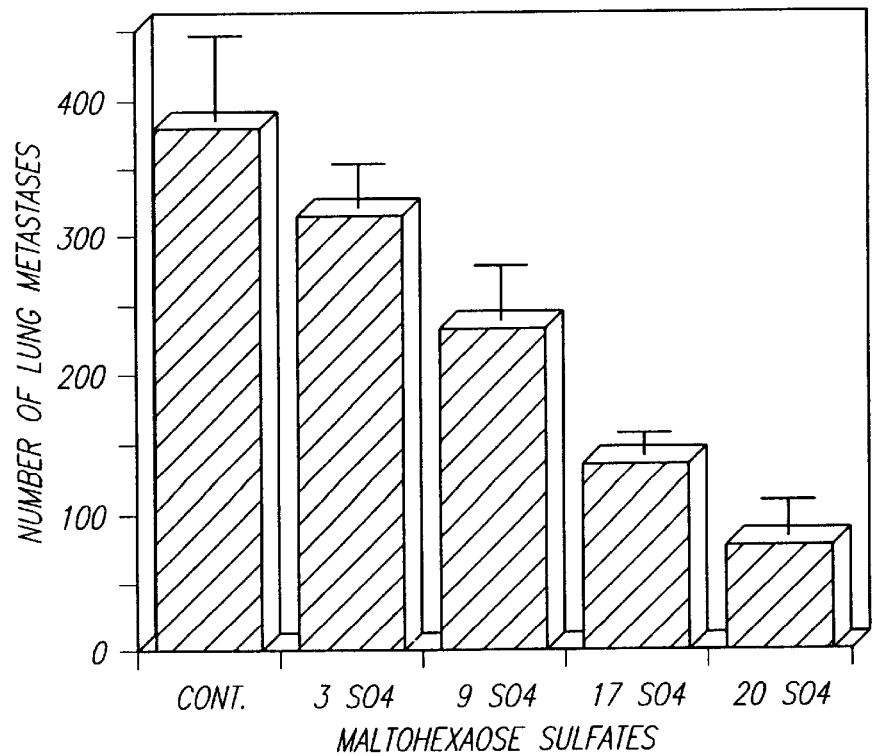

FIG. 6 shows the effect of degree of sulfation of maltohexaose sulfate on its ability to inhibit metastasis of the rat mammary adenocarcinoma 13762 MAT. Numbers along x-axis refer to number of sulfate groups/maltohexaose molecule. Control animals received tumour cells in the absence of compounds. The oligosaccharides were administered at a dose of 2 mg/rat, i.v., at the time of tumour cell injection. Vertical bars represent standard errors of means.

Figure 7:
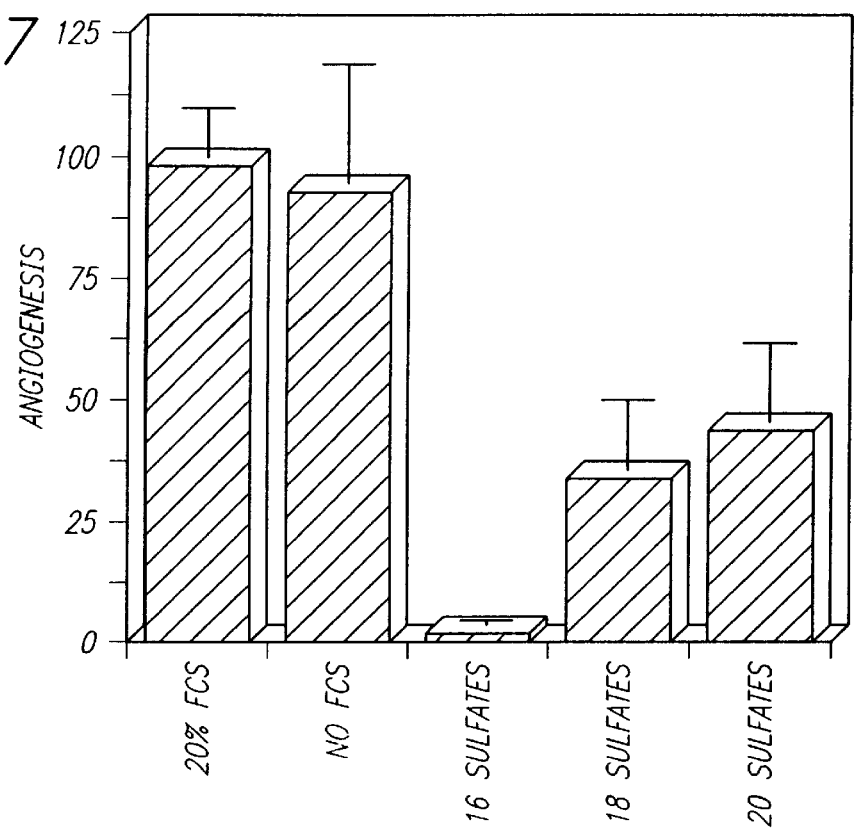
Figure 8:
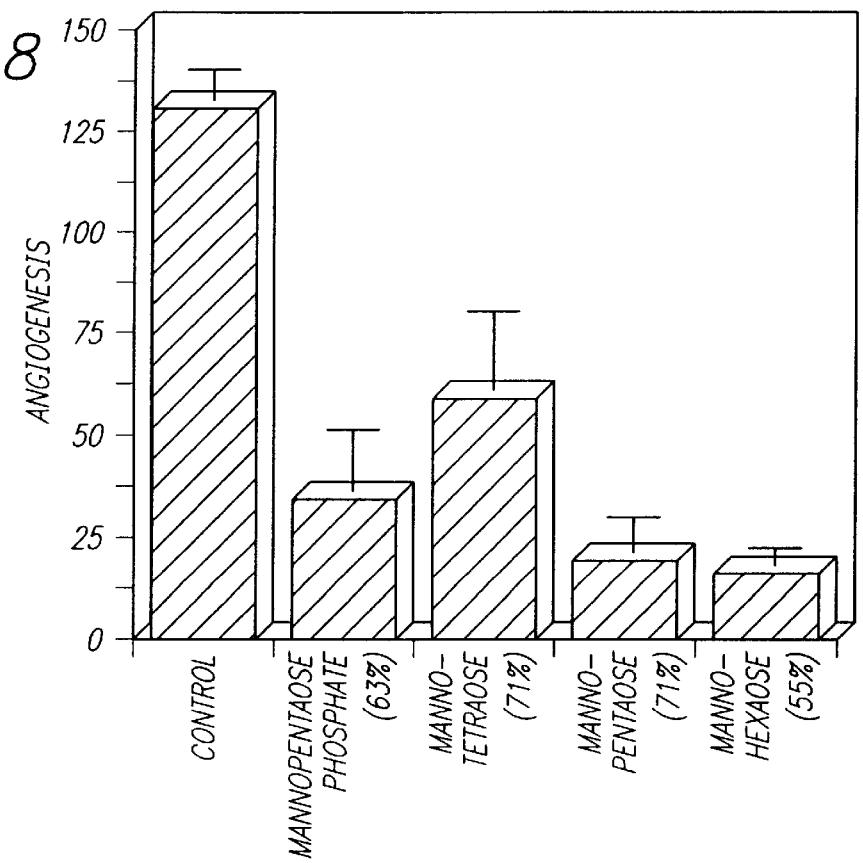
Figure 9:
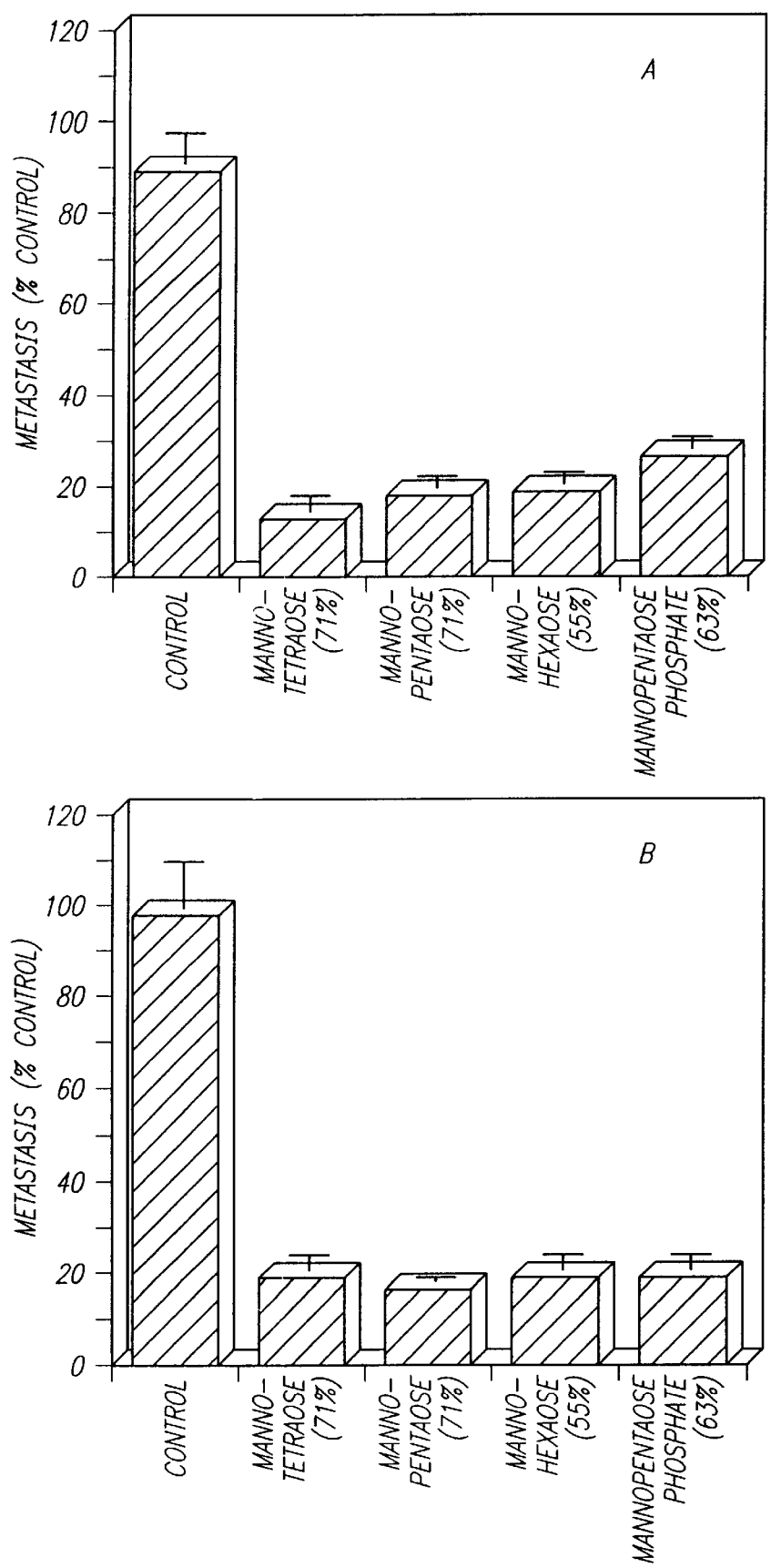

FIG. 7 shows the effect of maltohexaose with different numbers of sulfate groups/molecule on in vitro human angiogenesis. Oligosaccharides were added at 200 μg/ml and the assay was performed in serum free medium. A similar angiogenic response was observed in this experiment whether the assay was performed in serum containing (20% FCS) or serum free (no FCS) medium. Maltohexaose with 20 sulfates/molecule represents the maximally sulfated molecule. Data mean±standard error of four determinations FIG. 8 shows the effect of different mannose containing sulfated oligosaccharides on in vitro human angiogenesis. Values in brackets represents % sulfation of oligosaccharides. Oligosaccharides were added at 200 μg/ml and the assay was performed in serum containing medium. Data mean±standard error of four determinations FIG. 9 shows the effect of sulfated mannose oligosaccharides of different chain length on the metastasis of the rat mammary adenocarcinoma 13762 MAT. Values in brackets represent % sulfation of oligosaccharides. Control animals received 13762 MAT cells in the absence of oligosaccharide. Treated animals received either 2 mg (A) or 4 mg (B) subcut. of each compound immediately after the i.v. tumour cell injection. Vertical bars represent standard errors of the means.

Figure 10:
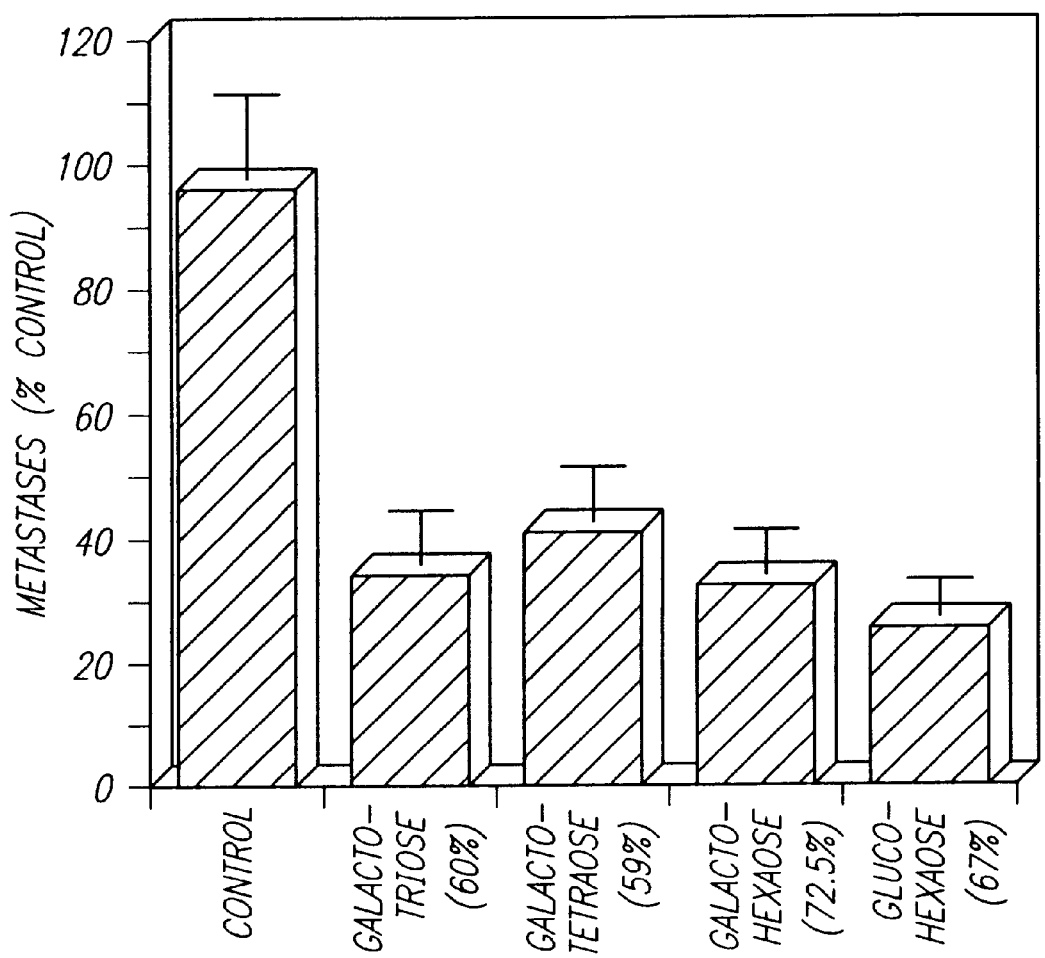

FIG. 10 shows the effect of sulfated galactose and glucose oligosaccharides of different chain length on the metastasis of the rat mammary adenocarcinoma 13762 MAT. Values in brackets represent % sulfation of oligosaccharides. Control animals received 13762 MAT cells in the absence of oligosaccharide. Treated animals received 2 mg subcut. of each compound immediately after the i.v. tumour cell injection. Vertical bars represent standard errors of the means.

EXAMPLE 1

Oligosaccharides of mannose were obtained in the following manner: 1,2,3,4-tetra-O-acetylmannose (31) (15.0 g, 43 mmol) and zinc chloride (1.5 g) were thoroughly mixed in tetramethylene-sulfone (7 ml), this mixture was heated under reduced pressure with stirring at ca. 110° C. for 6 hrs; at this point the reaction mass had hardened and vapour (acetic acid) generation had ceased. Throughout the time of reaction a sodalime tube was situated between the reaction vessel and the vacuum source. The reaction mixture was allowed to cool and a portion (11.0 g) of the product mixture was dissolved in dry pyridine (20 ml) and to this solution was added acetic anhydride (2 ml), this mixture was protected from atmospheric moisture and heated at ca. 50° C. with stirring for 2 hrs. After cooling, ethanol (10 ml) was added and the mixture allowed to stand for 2 hrs. The pyridine, ethanol and any ethyl acetate formed were evaporated off under reduced pressure and the residue washed extensively with water to remove zinc chloride, tetramethylenesulfone and pyridine. The residue was dissolved in dichloromethane, washed with water and the organic layer dried over anhydrous sodium sulfate. The derivatised oligosaccharides were initially separated into two fractions by applying the dichloromethane solution to a short column (4×40 cm) of silica gel 60 (130 g) which was first eluted with chloroform and then with acetone. Elution with chloroform gave a mixture of the fully acetylated monosaccharide and oligomers containing 3 to 5 units of mannose (Mixture A). Subsequent elution with acetone gave a mixture of fully O-acetylated oligomers containing mainly from 6 up to 12 mannose units per molecule (Mixture B).

Mixture A (4 g) was applied to a column (3.3×135 cm) packed with tic grade silica gel (H). The column was eluted with acetone/light-petroleum (bp 60–80°) with a gradient starting at 1:5 and increasing the percentage of acetone until a final ratio of 1:1 was reached. The flow rate was ≦0.5 ml/min. By collecting and pooling the appropriate fractions (determined by silica gel tlc analysis) and removing the solvent under reduced pressure fully O-acetylated mannose oligosaccharides 1a–1d were obtained as follows (n=number of mannose residues; yield, molecular rotation (c=2, CHCl$_3$)): 1a, (3; 0.7 g, 4.2%, $[\alpha]^{27}_D$=+ND); 1b, (4; 4.1 g, 8.4%, $[\alpha]^{27}_D$=+50); 1c, (5; 1.2 g, 7.9%, $[\alpha]^{27}_D$=+47.3); 1d, (6; 0.8 g, 5.2%, $[\alpha]^{27}_D$=+36.0). Mixture B (7.0 g) was chromatographed in a similar fashion to Mixture A but the elution gradient started with acetone/light-petroleum (bp 60–80°) 4:5 and the percentage of acetone increased until it was 100%. In this manner, the fully O-acetylated mannose oligosaccharides 1d–1j were obtained as follows (n=number of mannose residues; yield, molecular rotation (c=1, CHCl$_3$)): 1d, (6; 1.6 g, 10.4%, $[\alpha]^{27}_D$=+ND); 1e, (7; 3.2 g, 21.2%, $[\alpha]^{27}_D$=+50.0); 1f, (8; 0.5 g, 3.4%, $[\alpha]^{27}_D$=+47.0); 1g, (9; 0.7 g, 4.7%, $[\alpha]^{27}_D$=+59); 1h, (10; 0.9 g, 5.7%, $[\alpha]^{27}_D$=+54); 1i, (11; 0.02 g, 0.1%, $[\alpha]^{27}_D$=+ND); 1j, (12; 0.03 g, 0.2%, $[\alpha]^{27}_D$=+ND).

Compound 1a (1.55 g) was dissolved in dry methanol (40 ml) and 1M methanolic sodium methoxide (8.6 ml) was added with stirring at room temperature. The resulting precipitate was filtered off, washed thoroughly with methanol and dried. The product (2a; 0.61 g, 70% $[\alpha]^{27}_D$=+72°) was identified as mannotriose by elemental analysis (CHN values were ±0.4% of expected), electrospray mass spectrometry (M$^+$504) and nmr spectroscopy. Oligomers 1b–1j were treated similarly to give the following mannose oligosaccharides (n=number of mannose residues; yield % from acetylated derivatives, molecular rotation (c=1, H$_2$O)): 2b, (4; 75%, $[\alpha]^{27}_D$=+78°); 2c, (5; 85%, $[\alpha]^{27}_D$=+80°); 2, (6; 98%, $[\alpha]^{27}_D$=84°); 2e, (7; 98%, $[\alpha]^{27}_D$=86.3°); 2f, (8; 99%, $[\alpha]^{27}_D$=+98.0°); 2g, (9; 99%, $[\alpha]^{27}_D$=+106°); 2h, (10; 99%, $[\alpha]^{27}_D$=+100°); 2i, (11; 98% $[\alpha]^{27}_D$=ND); 2j, (12; 98%, $[\alpha]^{27}_D$=ND).

Alternatively these mannose oligosaccharides can be isolated by gel filtration (size exclusion) chromatography. Thus, a mixture of acetylated mannose oligosaccharides was obtained by heating a thoroughly stirred mixture of 1,2,3,4-tetra-O-acetylmannose (15.0 g, 43 mmol) and zinc chloride (1.5 g) in tetramethylene-sulfone (7 ml), under reduced pressure at ca. 110° C. for 6 hrs as described above. The reaction mixture was allowed to cool, and water (50 ml) added and the reaction mixture was stirred at room temperature for 5 min and the water layer discarded. This washing procedure was repeated and the mass was subsequently dissolved in chloroform, washed with water and dried over anhydrous sodium sulfate. After filtering, the chloroform was removed under reduced pressure to give the crude acetylated oligosaccharide mixture (11.3 g). This mixture was dissolved in isopropanol (20 ml) and methanol (60 ml) and then 1 M sodium methoxide in methanol (8 ml) was added and the mixture was allowed to stand at room temperature for 1 hour. The resulting precipitate was filtered off and washed twice with methanol (30 ml). After drying this product mixture (6.5 g) was applied to the top of a fine grade P2 gel (BioRad) gel filtration column (jacketed; 5×90 cm) which had been stabilised by running for two days with water (flow rate 0.5 ml per min) at 60° C. The column was eluted with water, at a flow rate of 0.5 ml per minute. Products eluting from the column were identified as peaks by differential refractometry and fractions collected accordingly. In this manner fractions corresponding to the areas under 11 separate peaks were collected. Each of these fractions was rechromatographed on an identical P2 gel column maintained at 60° C. and eluted with water at a flow rate of 0.5 ml/min. Thus, by way of example, the fraction identified as corresponding to mannopentaose (0.9 g) from the first gel filtration run was rechromatographed to give a main central peak with one shoulder on either side. The product eluting in the central peak was isolated by removing the water under reduced pressure to give (0.5 g) of material which was again rechromatographed on an identical P2 gel column at 60° C. at a flow rate of 0.3 ml/min. In this manner was obtained mannopentaose (0.3 g) identical with 2c above. Found C 38.4; H, 6.7, C$_{30}$H$_{52}$O$_{26}$. 6 H$_2$O requires C 38.5; H 6.8% Nitrogen value was 0% found and 0% expected.

The compound was found to be substantially pure by HPLC. This was determined on a Dionex HPLC system configured as follows:

Column: Code-CPMA1#1291 (+guard#1172). A Quarternary Ammonium Ion Exchange column.

Dectector: Electrochemical Detector (ED40:IAMP).

Flow rate: 1 ml/min.

Solvents: Solution A: 0.1M NaOH Solution B: 1M Acetate in 0.1MNaOH

| Gradient: | Time (min) | % A | % B | Action |
| --- | --- | --- | --- | --- |
| | 0 | 95 | 5 | Elution |
| | 20 | 90 | 10 | Elution |
| | 25 | 0 | 100 | Elution/Wash |
| | 30 | 0 | 100 | Elution/Wash |

Electrospray mass spectrometry showed this compound to have a mass M$^+$ of 828, the correct molecular weight of mannopentaose. In a similar manner mannotriose, mannotetraose, mannohexaose and mannoheptaose identical with 2a, 2b, 2d and 2e above were isolated.

EXAMPLE 2

This example shows the effect of carrying out the polymerisation reaction at a lower temperature than in Example 1. Oligosaccharides of glucose were obtained by polymerisation of 1,2,3,4-tetra-O-acetylglucose in the same manner as for mannose oligosaccharides produced by the method outlined in Example 1 above, except that in this case, the polymerisation reaction was carried out at 90° C. for 8 hours. The reaction mixture was treated as in Example 1 and the products were isolated by column chromatography, where the column (7 cm×155 cm) was packed with tlc grade silica gel (H). Using similar elution methods to those described in Example 1 the fully O-acetylated glucose oligosaccharides 3a–3e were obtained as follows (n=number of glucose residues; yield, molecular rotation (c=2,CHCl$_3$)): 3a, (3; 4.14 g, 24.9%, $[\alpha]^{27}_D$=+37.5°); 3b, (4; 2.92 g, 18.4%, $[\alpha]^{27}_D$=+44°); 3c, (5; 2.99 g, 19.1%, $[\alpha]^{27}_D$=+37.5°); 3d, (6; 1.37 g, 8.9%, $[\alpha]^{27}_D$=+36°); 3e, (7; 0.18 g, 1.2%, $[\alpha]^{27}_D$=+39°).

Compound 3a (1.0 g) was dissolved in dry methanol (30 ml) and 1M methanolic sodium methoxide (5.5 ml) was added with stirring at room temperature. The resulting precipitate was filtered off, washed thoroughly with methanol and dried. The product (4a; ($[\alpha]^{27}_D$=68.5°) was identified as glucotriose by elemental analysis, electrospray mass spectrometry (M$^+$=504) and nmr spectroscopy. Oligomers 4b–4e were treated similarly to give the following glucose oligosaccharides (n=number of glucose residues; % yield, molecular rotation (c=2, H$_2$O)): 4b, (4; 85%, $[\alpha]^{27}_D$=+83°); 4c, (5; 90%, $[\alpha]^{27}_D$=+84°); 4d, (6; 90%, $[\alpha]^{27}_D$=+86°); 4e, (7; 89%, $[\alpha]^{27}_D$=+92.5°).

Alternatively these glucose oligosaccharides can be isolated by gel filtration (size exclusion) chromatography. Thus, a mixture of acetylated glucose oligosaccharides was obtained following heating a thoroughly stirred mixture of 1,2,3,4-tetra-O-acetylglucose (15.0 g, 43 mmol) and zinc chloride (1.5 g) in tetramethylene-sulfone (7 ml), under reduced pressure at ca. 110° C. for 6 hrs as described above. The reaction mass was dissolved in dichloromethane, washed with water and dried over anhydrous sodium sulfate. The dichloromethane was removed under reduced pressure and the product was weighed and dissolved in isopropanol (20 ml) and methanol (60 ml) and then 1 M sodium methoxide in methanol (9 ml) was added and the mixture was allowed to stand at room temperature for 1 hour. The resulting precipitate was filtered off and washed twice with methanol (30 ml). A portion (7.6 g) of this mixture was dissolved in water (10 ml) and applied to a 5×90 cm water jacketed chromatography column packed with fine grade P2 size exclusion gel (BioRad). The column had been packed, preheated and run at 60° C. for two days prior to use. Following addition of the mixture of glucose oligosaccharides the column was maintained at 60° C. and eluted with water (1 ml/min). Products eluting from the column were identified as peaks by differential refractometry and fractions collected accordingly. In this manner fractions corresponding to the areas under 10 separate peaks were collected. Each of these fractions was rechromatographed on an identical P2 gel column at 60° C. and eluted with water at a flow rate of 0.5 ml/min. Thus, by way of example, the fraction identified as corresponding to glucopentaose (0.59 g) was rechromatographed to give a main central peak with one shoulder on either side. The product eluting in the central peak was isolated by removing the water under reduced pressure to give (0.3 g) of material which was again rechromatographed on an identical P2 gel column at 60° C. at a flow rate of 0.3 ml/min. In this manner was obtained glucopentaose (0.2 g) identical with 4c above. In a similar manner glucotriose, glucotetraose, glucohexaose and glucoheptaose identical with 4a, 4b, 4d and 4e above were isolated.

EXAMPLE 3

Oligosaccharides of other hexose sugars including galactose, altrose, talose, gulose, idose and allose can be obtained by following the methods disclosed in Examples 1 and 2.

For example, oligosaccharides of galactose were obtained in the following manner: 1,2,3,4-tetra-O-acetylgalactose (21.0 g) and zinc chloride (2.1 g) were thoroughly mixed in tetramethylene-sulfone (10 ml), this mixture was heated under reduced pressure with stirring at ca. 90° C. for 17 hrs; at this point the reaction mass had hardened and vapour (acetic acid) generation had ceased. Throughout the time of reaction a sodalime tube was situated between the reaction vessel and the vacuum source. The reaction mixture was allowed to cool, the reaction mass was subsequently dissolved in dichloromethane, washed with water and dried over anhydrous sodium sulfate. The dichloromethane was removed under reduced pressure and the product was weighed and dissolved in isopropanol (30 ml) and methanol (70 ml) and then 1 M sodium methoxide in methanol (10 ml) was added and the mixture was allowed to stand at room temperature for 1 hour. The resulting precipitate was filtered off and washed twice with methanol (30 ml). This mixture was separated by gel filtration chromatography as described for the mannose and glucose polymers in Examples 1 and 2 above. Products eluting from the column were identified as peaks by differential refractometry and fractions collected accordingly. In this manner 8 fractions were collected. Seven of these fractions were rechromatographed twice on an identical P2 gel column at 60° C. and eluted with water at a flow rate of 0.5 ml/min during the first run and 0.3 ml/min on the second. In this manner the following galactose oligosaccharides were obtained: galactotriose, 1.03 g, 5.3%; galactotetraose, 1.15 g, 6.0%; galactopentaose, 1.21 g, 6.3%; galactohexaose, 4.26 g, 22.1%; galactoheptaose, 2.11 g, 11%; galactooctaose, 1.91 g, 9.9% and galactononaose, 0.08 g, 0.4%.

EXAMPLE 4

To a solution of sulfur trioxide-pyridine complex (0.8 g) (Aldrich) in freshly distilled DMF (1 ml) at 80° C. was added dropwise a solution of mannopentaose (2c) (0.1 g) in dry pyridine (3 ml), and the whole was heated at 80° C. for a further 90 min. The supernatant was decanted while still warm and the sticky residue washed thoroughly with methanol (2 ml) three times. After decanting the residual methanol, the product was dissolved in water (5 ml) and neutralised (to pH~6) with barium acetate (approximately 0.4 g in 2 ml of water) with vigorous stirring. After centrifugation (3,000×g), the overlying liquid was decanted and retained and the precipitated barium sulfate pellet was washed thoroughly with water (3×10 ml). The retained overlying liquid and washings were combined and put onto a column (1.0×14 cm) of DOWEX 50W-X8-400 cation exchange resin ($H^+$ form). The column was eluted with water until the eluate was neutral. The eluate (~50 ml) was stirred and neutralised (to pH~7) with sodium acetate (0.7 g). The solution was diluted with acetone (200 ml) and centrifuged (1,750×g) to separate the product. The pellet was finely pulverised by crushing under methanol, and then stirred while still under methanol and then filtered off. The solid was washed several times with methanol to give the pure (inorganic salt-free) compound (0.2 g; 66%). The product was not contaminated with barium ion (by micro analysis and flame ionisation) nor nitrogen (micro analysis).

The product, sulfated mannopentaose, was found to have 11 out of a possible 17 positions sulfated. Found C 14.2; H, 3.0; S 14.1; Na 7.3. $C_{30}H_{60}O_{59}S_{11}Na_8$. 36 $H_2O$ requires C 14.1; H 5.2; S 13.8; Na 7.2%. Nitrogen and barium values were 0% found and 0% expected.

EXAMPLE 5

To a mixture of sulfur trioxide-pyridine complex (Aldrich Chemical Company) (4 g) in dry DMF (5 ml) was added dry pyridine (10 ml) under a dry nitrogen atmosphere. This mixture was warmed to 50° C. and stirred rapidly while glucohexaose (4d) (0.5g), isolated by the method described in Example 2 above, was added in a single addition. Additional pyridine (5 ml) was added and the mixture was then heated, with continuous stirring at 80° C. for 90 minutes. The reaction mixture was then kept at 4° C. overnight. The liquid was decanted from the reaction vessel, methanol (3 ml) was added and the semi-solid mass was broken up and mixed thoroughly with the methanol. After settling the methanol was decanted and this procedure was repeated. Water (5 ml) was added to the remaining solid and the resulting solution placed into a 50 ml test tube. The reaction vessel was rinsed with additional water (5 ml) which was combined with the first solution. The resulting solution was adjusted to pH ca. 7–8 with 40% NaOH, after which methanol (40 ml) was added. The resulting cloudy solution was centrifuged (3,000×g) for 25 min. and the clear solution decanted from the precipitate. The remaining solid was again dissolved in water (10 ml), methanol (40 ml) added, and the tube centrifuged as before. After decanting the clear overlaying solvent, the solid was dissolved in water (10 ml)

and run through a P2 gel desalting column (2.5 cm×250 cm; fine grade P2 gel -BioRad) to give the expected sodium salt of the sulfated derivative of 1,6-glucohexaose.

EXAMPLE 6

Although synthesis of hexose homopolymers is described in Examples 1, 2 and 3, it is usually extremely difficult to synthesise most oligosaccharide structures. Thus, a simpler approach is to sulfate oligosaccharides of defined structure from natural sources. The natural product oligosaccharides used in this example were of two classes. The first class contained oligosaccharides which required no further degradation and fractionation. Examples of this class are maltose, raffinose and stachyose. The second class consisted of oligosaccharides obtained from naturally occurring polysaccharides which were partially degraded enzymatically or chemically, and size fractionated. Examples of this class are the amylose-, chondroitin- and dextran-derived oligosaccharides and mannopentaose phosphate from the yeast *Pichia holstii*.

Maltose, raffinose and stachyose were purchased from Sigma Chemical Co, St Louis, Mo. Maltotriose, maltotetraose, maltopentaose, maltohexaose and maltoheptaose were obtained from Seikagaku, Tokyo, Japan and represent oligosaccharides purified from limited amylase digests of the α1–4 linked glucose homopolymer, amylose. The chondroitin tetra-, hexa- and octasaccharides were purified by gel filtration fractionation of a bovine testicular hyaluronidase digest of chondroitin-6-sulfate as previously described (32). The cyclohexa-, hepta- and octa-amyloses were obtained from Sigma. These oligosaccharides may be sulfated as described in Example 5.

By way of example, maltohexaose sulfate was prepared in the following manner. To a solution of sulfur trioxide-pyridine complex (4.0 g) (Aldrich) in freshly distilled DMF (5 ml) at 80° C. was added dropwise a solution of maltohexaose (0.5 g) in dry pyridine (15 ml), and the whole was heated at 80° C. for a further 90 min. The supernatant was decanted while still warm and the sticky residue washed thoroughly with methanol (10 ml) three times. After decanting the residual methanol, the product was dissolved in water (15 ml) and neutralised (to pH~6) with barium acetate (ca. 2.0 g in 10 ml of water) with vigorous stirring. After centrifugation (3,000×g), the overlying liquid was decanted and retained and the precipitated barium sulfate pellet was washed thoroughly with water (3×10 ml). The retained overlying liquid and washings were combined and put onto a column (2.5×14 cm) of DOWEX 50W-X8-400 cation exchange resin (H$^+$ form). The column was eluted with water until the eluate was neutral. The eluate (~250 ml) was stirred and neutralised (to pH~7) with sodium acetate (3.5 g). The solution was diluted with acetone (1 L) and centrifuged (1750×g) to separate the product. The pellet was finely pulverised by crushing under methanol, and then stirred while still under methanol and then filtered off. The filtrate was washed several times with methanol to give the pure (inorganic salt-free) compound (0.88 g; 55%). The product was not contaminated with barium ion (determined by micro analysis and flame ionisation) nor nitrogen (micro analysis).

This product was found to have 14 our of a possible 20 positions sulfated. Found C 13.9; H 2.2; S 14.3; Na 6.7. $C_{36}H_{71}O_{73}S_{14}Na_9$. 45 $H_2O$ requires C 13.8; H 5.1; S 14.3; Na 6.6%. Nitrogen and barium values were 0.32 and 0% found respectively and 0% expected for each. $^1$H NMR data (300 MHZ—Gemini 300; referenced from acetone 2.25 ppm down field from TMS); for the above maltohexaose sulfate indicated that 14 of a possible 20 positions were sulfated. This was determined from the chemical shifts of the hydrogens centred around 4.15 ppm (integrating for 20 H) vs those centred around 4.4 ppm (integrating for 16 H). It can be assumed that all of the primary OH groups, i.e. those at position 6, will be sulfated since this is the least sterically hindered position. It is further assumed that in the internal sugar residues only one other position will be sulfated. The terminal sugar residues, in addition to the one on position 6, will each have two other positions sulfated.

Mannopentaose phosphate was prepared from the exopolysaccharide produced by the diploid yeast *Pichia holstii* (strain NRRL Y-2448 formerly *Hansenula holstii*.). The method for the growth of *P. holstii* and isolation of mannopentaose phosphate was based on that described previously (33, 34). Briefly, the crude exopolysaccharide was isolated from aerobically grown yeast culture supernatants as a potassium salt by ethanol precipitation. Acid hydrolysis was then used to liberate the mannopentaose phosphate from the phosphomannan monoester core (PPME) of the exopolysaccharide. PPME and the mannopentaose phosphate were then separated from each other as barium salts by differential ethanol precipitation and subsequently by gel filtration. The oligosaccharide has the structure P-6-Man-α-(1→3)-Man-α-(1→3)-Man-α-(1→3)-Man-α-(1→2) Man (34).

The sulfate of the yeast mannopentaose phosphate (33,34) isolated from the exopolysaccharide of yeast was prepared in the following manner. A suspension of yeast mannopentaose phosphate (0.09 g) in DMF (2 ml) and pyridine (3 ml) was added to a solution of sulfur trioxide-pyridine complex (0.8 g) (Aldrich) in DMF (1 ml). The mixture was heated at 80° C. for 2 hours. The supernatant was decanted while still warm and the sticky residue washed thoroughly with methanol (2 ml) three times. After decanting the residual methanol, the product was dissolved in water (5 ml) and neutralised (to pH 6) with barium acetate (approximately 0.7 g in 5 ml of water) with vigorous stirring. After centrifugation (3,000×g) the overlying liquid was decanted and the precipitated barium sulfate pellet was washed thoroughly with water (3×10 ml). The overlying liquid and washings were combined and put onto a column (2.5×14 cm) of DOWEX 50W-X8-400 cation exchange resin (H$^+$ form). The column was eluted with water until the eluate was neutral. The eluate (ca 50 ml) was stirred and neutralised (to pH 7) with sodium acetate (ca 0.4 g). The solution was diluted with acetone (150 ml) and centrifuged (1,750×g) to separate the product. The pellet was finely pulverised by crushing under methanol, and stirred while still under methanol and then filtered off. The solid was washed several times with methanol to give the sulfated yeast mannopentoase phosphate (0.18 g). The product was not contaminated with barium ion (determined by micro analysis and flame ionisation) nor nitrogen (micro analysis).

This product was found to have 10 out of a possible 16 positions sulfated. Found C 15.35; H 2.7; P 1.2; S 13.7; Na 8.5. $C_{30}H_{41}O_{59}PS_{10}Na_9$. 25 $H_2O$ require C 15.3; H 3.5; P 1.3; S 13.6; Na 8.8%. Nitrogen and barium values were 0.16 and 0% found respectively and 0% expected for each.

1,6-α-Glucose oligosaccharides were prepared by acid hydrolysis of dextran (average MW 71,000; Sigma Chemical Co.). Thus, dextran (5 g) was dissolved in distilled water (100 ml) and this solution was adjusted to pH 1.8 with 1M hydrochloric acid. The mixture was refluxed (100° C.) for 48 hours. The mixture was dried under reduced pressure and made up to 100 ml with distilled water and dried a second time under reduced pressure. Absolute ethanol (100 ml) was added to the residue and evaporated off under reduced pressure. The residue was made up to 4 ml with distilled water and applied to a 5×90 cm water jacketed chromatography column packed with fine grade P2 size exclusion gel (BioRad). The column had been packed, preheated and run at 60° C. for two days prior to use. Following addition of the mixture of 1,6-α-glucose oligosaccharides the column was maintained at 60° C. and eluted with water (1 ml/min). Products eluting from the column were identified as peaks by differential refractometry and fractions collected accordingly. In this manner fractions corresponding to the areas under separate peaks were collected. Each of these fractions was rechromatographed on an identical P2 gel column at 60° C. and eluted with water at a flow rate of 0.5 ml/min. Thus, by way of example, the fraction identified as corresponding to 1,6-α-glucohexaose (0.19 g) was rechromatographed to give a main central peak with one shoulder on either side. The product eluting in the central peak was isolated by removing the water under reduced pressure to give (0.16 g) of material which was again rechromatographed on an identical P2 gel column at 60° C. at a flow rate of 0.3 ml/min. In tis manner was obtained glucohexaose (0.14 g) (electrospray $M^+=990$). In a similar manner 1,6-α-glucotriose, 1,6-α-glucotetraose (0.21 g) and 1,6-α-glucopentaose (0.17 g) were isolated.

EXAMPLE 7

A. Materials and Methods

Anticoagulant Activity of Sulfated Oligosaccharides

The anticoagulant activity of each sulfated oligosaccharide was assessed as previously described (35), using both thrombin time and activated partial thromboplastin time procedures. The activity of each preparation was compared with a heparin control and anticoagulant activity expressed as a percentage of heparin activity.

Human Angiogenesis Assay

The assay method used is described in International Patent Application No. PCT/AU95/00105, the disclosure of which is incorporated herein by reference. Blood vessels, approx 1–2 mm in diameter and 2–5 cm in length, were excised from the surface of human placentas within 6 hours of birth. The vessels were placed in Hank's BSS containing 2.5 mg/ml of fungizone and cut into 1–2 mm length fragments using fine dissecting forceps and iridectomy scissors. Vessel fragments were freed of residual clots and soaked in Hank's BSS before use. Dissecting and sectioning of vessels was performed with the aid of a magnifier lamp (Maggylamp, Newbound, Balmain, NSW, Australia). Similar angiogenic responses were obtained from blood vessels of venular and arterial origin but, for each assay, vessel fragments from only one vessel were used.

Angiogenesis assays were performed in 24 or 48 well culture plates (Costar, Cambridge, Mass.). In the 24 well format, 30 μl of bovine thrombin (50 NIH units/ml in 0.15 M NaCl; Sigma Chemical Co., St Louis, Mo.) was added to each well followed by 1.0 ml/well of 3 mg/ml bovine fibrinogen (Sigma) in Medium 199. The thrombin and fibrinogen were mixed rapidly and one vessel fragment quickly placed in the centre of the well before clot formation. Usually fibrin gel formation occurred in 30 seconds and the vessel fragment was left suspended in the gel. Following gel formation 1.0 ml/well of Medium 199 supplemented with 20% foetal calf serum (FCS), 0.2 mg ε-amino caproic acid, L-glutamine and antibiotics (gentamycin and fungazone) was added. In the 48 well format all reagent volumes were halved. Vessels were cultured at 37° C. in a humidified environment for 14–21 days with the medium being changed twice weekly. Angiogenesis was quantified by computer based image analysis, using NIH Image software, of digital images of the cultures obtained with a Dycam digital camera mounted on an inverted microscope (Olympus, Tokyo, Japan).

Heparanase Assay

The heparanase assay is based on the observation that the serum protein, histidine-rich glycoprotein (HRG), binds to heparan sulfate chains and masks the heparanase cleavage site. Based on the finding that heparanase-cleaved heparan sulfate fails to bind to HRG a heparanase assay has been developed which involves digesting $^3$H-labelled heparan sulfate chains with heparanase, binding the digested heparan sulfate to HRG coupled beads and measuring unbound $^3$H label. With increasing digestion of the substrate an increasing amount of $^3$H label fails to bind to the HRG beads. Thus, this method represents a simple and rapid procedure for measuring heparanase activity in tissue extracts and assessing heparanase inhibition by various compounds.

Initially, bovine intestinal heparan sulfate (Mr av 32 kDa) was partially de-N-acetylated by heating in hydrazine hydrate (36) and re-acetylated with $^3$H-acetic anhydride. Chicken HRG, purified by the method of Rylatt et al (1981) (37), was coupled to CNBr activated Sepharose 4B (Pharmacia) according to the manufacturers instructions.

Human platelet heparanase activity was determined by incubation (37° C., 30 min) of purified human platelet heparanase (which has been shown to have the same activity towards heparan sulfate as heparanase activity present in highly metastatic cultured human carcinoma HCT 116, rat adenocarcinoma 13762 MAT and mouse melanoma B16 cell lines) with 60 pmoles $^3$H-radiolabelled bovine intestinal heparan sulfate. Activity was determined by the rate of production of smaller (approx 5 kDa) heparan sulfate fragments that were not bound following passage of the incubation mixture (100 μl) through HRG-Sepharose minicolumns (200 μl packed beads) which retained the larger uncleaved and partially cleaved substrate.

In heparanase-inhibition assays, different concentrations of inhibitor were added to the enzyme prior to addition of radiolabelled substrate, the inhibitor being retained in the reaction mixture throughout the incubation period.

Metastasis Assay

The antimetastatic activity of the different sulfated oligosaccharides was assessed using the highly metastatic rat mammary adenocarcinoma 13762 MAT (35). The tumour cells were maintained in vitro as previously described (35). Female Fisher 344 rats, (10–13 weeks of age) were injected i.v. with $2 \times 10^5$ 13762 MAT cells in 0.6 ml RPMI 1640 medium containing 10% FCS. At the time of tumour cell injection animals were also injected with 2 mg of sulfated oligosaccharide, similar results being obtained if the oligosaccharide was injected i.v., i.p. or subcut. Lungs were removed from the rats 13 days following tumour cell injection, placed in Bouin's solution for at least 24 hours and lung metastases then assessed under a dissecting microscope. The number of lung metastases in sulfated oligosaccharide treated rats was compared with that observed in control animals, with a minimum of four animals being included in each group.

Effect of Sulfated Oligosaccharides on the FGF-Heparin/Heparan Sulfate Interaction A binding assay, which is described in detail elsewhere (38), was used to measure the binding of aFGF and bFGF to heparin and assess the ability of the different sulfated oligosaccharides to inhibit this interaction. Briefly, FGFs were immobilised in the wells of 96 well PVC plates and the binding of radiolabelled heparin to the immobilised FGFs assessed. In inhibition assays serial dilutions of sulfated oligosaccharides were examined for their ability to inhibit the FGF-heparin interaction. Inhibition results were expressed as the concentration of sulfated oligosaccharide required to inhibit heparin binding to the immobilised FGFs by 20% or 50%. Unlabelled heparin was included as a control in all binding-inhibition experiments.

The FGF-heparan sulfate interaction was assessed, as reported earlier (39), by measuring the binding of BALB/c 3T3 fibroblasts to PVC immobilised FGFs, cell binding being detected by Rose Bengal staining of adherent cells. Sulfated oligosaccharides were examined for their ability to inhibit this cell adhesion process, which is totally dependent upon heparan sulfate structures on the surface of BALB/c 3T3 cells (39). Data was expressed as the concentration of sulfated oligosaccharide which inhibited cell adhesion by 50% (IC50).

Air Pouch Inflammation Model

The assay is based on a previously reported procedure (40). Subcutaneous air pouches were formed on the backs of mice by injecting 5 ml of sterile air below the skin of a shaved area between the scapulae of an anaesthetised mouse on day 1. On day 3 the pouch was reinflated by the injection of 2.5 ml of air. Inflammation was induced on day 6 by injecting directly into the pouch 1.0 ml of 56 mg/ml thioglycollate or 1.0 ml of saline as a control. Approximately 17–20 hrs after thioglycollate injection the animals were killed by cervical dislocation and the cellular contents of the pouch retrieved by the injection of 2.5 ml of ice cold PBS/5% FCS. Sulfated oligosaccharides were tested for their ability to inhibit the inflammatory reaction by being injected subcut. (50 $\mu$l in PBS) in a separate site immediately following administration of the thioglycollate. Prednisolone was used as a control anti-inflammatory drug, being injected subcut. in oil at 25 mg/kg. The total cellular contents of each pouch was determined using a Coulter Counter and different leukocyte subpopulations were assessed by immunofluorescent flow cytometry.

Mouse Asthma Model

A previously reported mouse model of asthma (41) was used to test the ability of the sulfated oligosaccharides to inhibit aeroallergin (ovalbumin, OVA) induced eosinophil infiltration into lungs. Mice (C57BL/6, 6–10 wk of age) were sensitised by i.p. injection with 50 mg OVA/1 mg Alhydrogel (CSL Ltd, Parkville, Australia) in 0.9% sterile saline on days 0 and 12. On day 24, the mice were exposed to an aerosol of OVA (10 mg/ml) in 0.9% saline for 30 min three times (at 1 hr intervals), and then exposed to a similar challenge on days 26 and 28. The aerosol was generated at 6 litres/min by a nebuliser that produced a mean particle diameter of 39 $\mu$m into a closed chamber of 800 cm$^3$. On day 29 the mice were killed by cervical dislocation. Tracheae were cannulated and the airways lumina were washed with 4×1 ml of 0.9% saline containing BSA (0.1% wt/vol) at 37° C. Approximately 0.8 ml of the instilled fluid was recovered per wash. The bronchoalveolar lavage fluid (BALF) obtained from one animal was pooled and cell numbers were determined using a standard haemocytometer. BALF cells were also cytocentrifuged and differentially stained with May-Grunwald-Giemsa solution, eosinophils being identified using morphological criteria. Data was calculated as number of eosinophils/ml of BALF. Sulfated oligosaccharides were administered to the animals either systemically by i.p. inserted ALzet miniosmotic pumps or via the lungs as an aerosol. Miniosmotic pumps were inserted on day 23, 24 hr before OVA challenge, and continually delivered drug until animals were sacrificed on day 29. In the case of aerosol delivery, mice were exposed to an aerosol of sulfated oligosaccharides in 0.9% saline for 30 min three times (at 1 hr intervals) on days 23, 25 and 27.

Experimental Autoimmune Encephalomyelitis (EAE) Model

Spleen cells were prepared for the adoptice transfer of EAE as previously described (43). Briefly, Lewis rats were sensitised to myelin basic protein, the immune spleen cells activated by ConA in vitro and 30×10$^6$ ConA activated EAE effector cells transferred i.v. to each recipient. Miniosmotic pumps (Alzet) containing sulfated oligosaccharides were implanted subcut at the time of cell transfer and delivered a dose of 70 mg/kg/day for 14 days. Clinical EAE was graded according to the following scheme: 0, asymptomatic; 1, flaccid distal half of tail; 2, entire tail flaccid; 3, ataxia, difficulty in righting; 4, hind limb weakness; and 5, hind limb paralysis.

Inflammatory Bowel Disease Model

Inflammatory bowel disease was induced in mice by the supplementation of the drinking water with 5% (w/v) dextran sodium sulphate (DSS) as suppled by TdB Consultancy, Uppsala, Sweden. The solution was adjusted to pH 8.0 and filtered through a 0.45$\mu$ media membrane. DSS solutions were collected daily, refiltered and volumes adjusted with fresh DSS stock. Male BALB/c mice of 6–7 weeks of age were screened by body weight and those between 20–23 gm were grouped into cages of 5 mice/cage.

Mice were injected with sulfated mannopentaose phosphate (20 mg/kg/day) or vehicle (sterile water) at 8 hourly intervals from day 0 until day 10. The injection volume was standardised to 100 $\mu$l and injected subcutaneously in the nape of the neck.

The DSS consumption rate, body weight and symptoms were scored daily for all mice. The diarrhoea and rectal bleeding symptoms were each scored as either slight or gross and given numerical values of 1 and 4, respectively. The presence of mucus was also noted and included as a slight diarrhoea score. The sum of the diarrhoea and rectal bleeding scores was then divided by the number of surviving animals in that group on that day. The total score is the sum of both diarrhoea and rectal bleeding scores.

B. Results

Anti-Angiogenic and Anti-Metastatic Activity of Sulfated Naturally Occurring Oligosaccharides Once a range of sulfated naturally occurring oligosaccharides had been synthesised they were examined in a range of biological assays. Table 1 summarises the results obtained with the sulfated forms of 12 naturally occurring oligosaccharides. The biological activities of suramin, (a compound which has moderate anti-angiogenic and heparanase inhibitory activity) (42), and heparin are also included in Table 1 for comparison.

Initially it was shown that all the sulfated oligosaccharides tested had negligible anticoagulant activity, ie <2% activity of heparin (Table 1). This was an important property as heparin, a potent antimetastatic compound, has limited clinical utility for this indication due to its potent anticoagulant activity.

Three of the sulfated naturally occurring oligosaccharides were quite potent inhibitors of human angiogenesis, namely sulfated mannopentaose phosphate (P. holstii derived), maltotetraose sulfate and maltohexaose sulfate. Mannopentaose phosphate and maltohexaose were the most potent of these compounds with a 50% inhibitory concentration of 2 $\mu$g/ml, whereas maltotetraose gave 50% inhibition at 20 $\mu$g/ml. An example of the pronounced inhibition of angiogenesis induced by 20 μg/ml of maltohexaose sulfate is depicted in FIG. 1. It is interesting to note that heparin had little anti-angiogenic activity. Thus, it appears likely that sulfated oligosaccharides of relatively short chain length are required for this type of activity. A more complete titration of angiogenesis inhibition by the maltose series is depicted in FIG. 2 and by sulfated mannopentaose phosphate in FIG. 3. It can be seen that, with the maltose series, maltose sulfate had little inhibitory activity whereas maltotetraose and maltohexaose sulfate were quite potent inhibitors (FIG. 2).

All of the angiogenesis experiments presented in Table 1 involved the addition of oligosaccharide to the culture medium at the commencement of the angiogenesis assay. However, preliminary studies (data not shown) indicate that addition of maltohexaose sulfate, after commencement of the angiogenesis response, can also inhibit further vessel outgrowth although most effective inhibition occurs when the compound is added at culture commencement.

The sulfated oligosaccharides also differed markedly in their heparanase inhibitory activity, the most potent inhibitors being sulfated mannopentaose phosphate and maltohexaose sulfate, the activity of these two compounds resembling that of heparin (Table 1). Interestingly, these two compounds are also effective anti-angiogenic compounds. However, angiogenesis inhibition did not correlate with the heparanase inhibitory activity of many compounds. For example, the sulfated cycloamyloses were quite potent heparanase inhibitors but poor angiogenesis inhibitors. The maltose series was also very informative regarding chain length and heparanase inhibition. Table 3 presents the heparanase inhibitory activity for the complete maltose series, ranging from the disaccharide (maltose) to the heptasaccharide (maltoheptaose). Maltose was non-inhibitory, maltotriose was weakly inhibitory, maltotetraose exhibited modest inhibiting activity, whereas the penta-, hexa- and hepta-saccharides exhibited high inhibitory activity. Thus, a sulfated pentasaccharide or greater is required for optimal heparanase inhibition.

Many of the sulfated sugars have also been tested in vivo for anti-metastatic activity (Table 1). In general, there is a reasonably good correlation between heparanase inhibition and antimetastatic activity. Thus, sulfated mannopentaose phosphate and maltohexaose sulfate, the two compounds with the highest heparanase inhibitory activity, exhibit the greatest antimetastatic activity, in fact, they do not differ significantly from heparin in their ability to prevent metastasis (Table 1). Two other compounds, cyclo-octa-amylose sulfate and stachyose sulfate were also reasonably effective antimetastatics, a property consistent with their modest heparanase inhibitory activity. Collectively these data suggest that sulfated mannopentaose phosphate and maltohexaose sulfate simultaneously possess considerable anti-angiogenic, antimetastatic and heparanase inhibitory activities.

The antimetastatic activity of the maltose series of sulfated oligosaccharides is presented in greater detail in FIG. 4. With increasing chain length there was a steady increase in the antimetastatic activity of the oligosaccharides with the penta-, hexa- and hepta-saccharides being the most active. When administered intravenously at a dose of 2 mg/rat, maltose sulfate had no effect on metastasis (FIG. 4A) but when given subcutaneously at 4 mg/rat significant metastasis inhibition was observed (FIG. 4B). Subsequent experiments revealed that, irrespective of the route of injection (ie, i.v., subcut. or i.p.), sulfated oligosaccharides exhibited comparable antimetastatic activity (data not shown). In fact, the antimetastatic activity of maltose sulfate was only observed when high doses were administered to animals. Since maltose sulfate is a very poor heparanase inhibitor this result suggests that heparanase inhibition may not be the only way the sulfated oligosaccharides inhibit tumour metastasis, particularly when high doses of the oligosaccharides are used.

Cycloamyloses were sulfated and included in the study as they represent non-linear oligosaccharides. It is interesting to note that these compounds were only modestly active (Table 1), implying that linear oligosaccharides may be required for optimum activity. Furthermore, the most active sulfated oligosaccharides were much more effective inhibitors of angiogenesis, metastasis and heparanase activity than suramin (Table 1), a drug currently undergoing clinical trials as an anti-angiogenic compound (42).

Since the anti-angiogenic activity of the compounds did not always directly correlate with their heparanase-inhibitory activity, it seemed likely that the sulfated oligosaccharides could inhibit angiogenesis by some other mechanism. As mentioned above, it is highly likely that some sulfated oligosaccharides can perturb the action of angiogenic growth factors by disrupting growth factor—heparan sulfate interactions. Previous analyses (see International Patent Application No. PCT/AU95/00105) have shown that the human angiogenesis assay used in this Example is largely dependent upon endogenous bFGF, and to a lesser extent upon aFGF and VEGF action. Thus, the various sulfated oligosaccharides were examined for their ability to act as competitors of the interaction of bFGF, aFGF and VEGF with heparin or heparan sulfate.

It was found that, with increasing chain length, the maltose series of sulfated oligosaccharides became more effective inhibitors of the interaction of bFGF and aFGF with cell surface heparan sulfates (Table 2), ie, maltose was weakly inhibitory, whereas the penta-, hexa- and hepta-saccharides were the most active. Sulfated mannopentaose phosphate also exhibited considerable inhibitory activity in this system (Table 2). The complete inhibition curves for the inhibition of the aFGF-heparan sulfate interaction by the maltose series of sulfated oligosaccharides is presented in FIG. 5. Additional studies showed that maltohexaose sulfate was also a potent inhibitor of the binding of radiolabelled heparin to bFGF and aFGF (data not shown).

Since maltohexaose sulfate was one of the most active anti-angiogenic and antimetastatic compounds, the influence of degree of sulfation on its biological activity was examined in some detail. Initially it was noted that even though some anticoagulant activity was detected with the most highly sulfated maltohexaose, this activity was still extremely low when compared with heparin (Table 2). With increasing sulfation, however, there was a steady increase in the ability of maltohexaose to inhibit heparanase activity and FGF binding to heparan sulfate (Table 2). However, inhibitory activity plateaued in both systems when sulfation was 85% or greater.

Metastasis inhibition studies (FIG. 6) also demonstrated that with increasing degrees of sulfation, maltohexaose sulfate became a more effective antimetastatic drug. In contrast, there was a suggestion that very highly sulfated maltohexaose (90–100% sulfated) was a less effective inhibitor of angiogenesis (FIG. 7). These data suggest that there are subtle differences in the optimum sulfated oligosaccharide structure required to inhibit angiogenesis and metastasis. Nevertheless, a number of sulfated oligosaccharides, derived from naturally occurring oligosaccharides, have been identified which simultaneously exhibit potent antimetastatic and anti-angiogenic activity.

These compounds are sulfated mannopentaose phosphate from P. holstii and maltopentaose, -hexaose and -heptaose sulfate.

Anti-Angiogenic and Anti-Metastatic Activity of Sulfated Synthetic Oligosaccharides The sulfated synthetic oligosaccharides described in Examples 1–5 were also tested for their biological activity. Table 3 summarises the ability of sulfated synthetic oligosaccharides containing mannose, galactose or glucose to inhibit coagulation, heparanase action and growth factor—heparan sulfate binding. All of the synthetic sulfated oligosaccharides tested exhibited negligible anticoagulant activity. However, with the exception of the trisaccharides of mannose and glucose, all the other sulfated oligosaccharides were reasonably effective inhibitors of heparanase activity and growth factor—heparan sulfate binding. In fact, the overall conclusion is that sulfated synthetic oligosaccharides containing 4–6 hexose units (ie D-mannose, D-galactose or D-glucose) are highly active in these assays. An exception is galactotriose sulfate, which was essentially as active as other members of the galactose series.

When tested in the human angiogenesis assay the sulfated mannose oligosaccharides were inhibitory, although the penta- and hexa-saccharides were more active than the tetrasaccharide (FIG. 8), resembling sulfated mannopentaose phosphate in their efficacy. Similarly, the sulfated mannose tetra-, penta- and hexa-saccharide were as effective as sulfated mannopentaose phosphate as antimetastatic drugs (FIG. 9). The galactose containing sulfated oligosaccharides and glucohexaose sulfate also inhibited metastasis (FIG. 10), although they tended to be slightly less active than the mannose containing compounds.

Anti-Inflammatory Activity of Sulfated Oligosaccharides

As mentioned above, a key barrier to the entry of leukocytes into inflammatory sites is the subendothelial basement membrane. In order to traverse this membrane, leukocytes must employ a battery of degradative enzymes (11). Of particular relevance is the endoglycosidase, heparanase, which cleaves basement membrane associated heparan sulfate chains and is essential for leukocyte extravasation (12, 13). In fact, as with metastasis-inhibition studies (35), sulfated polysaccharides which inhibit heparanase activity are potent inhibitors of inflammation (43, 44). Based on these observations, it would be anticipated by those skilled in the art, that the sulfated oligosaccharides which were potent anti-angiogenic and antimetastatic agents would be very effective anti-inflammatory compounds. Of particular importance in this regard are maltohexaose sulfate and mannopentaose sulfate. Furthermore, since angiogenesis is associated with chronic inflammatory diseases such as rheumatoid arthritis (18), the antiangiogenic activity of these compounds would be of additional value in the treatment of inflammation.

Evidence in favour of this prediction has been obtained in several animal models of inflammation. First, maltohexaose sulfate, mannopentaose sulfate and sulfated mannopentaose phosphate were able to significantly inhibit thioglycollate-induced air pouch inflammation (Table 4). In fact, in one experiment a single injection of mannopentaose sulfate was as effective as prednisolone at inhibiting the leukocyte infiltration, which was predominantly neutrophil in nature, whereas maltohexaose sulfate was somewhat less effective. Even greater inhibition of the inflammatory response was observed when the sulfated oligosaccharides were injected in two equal doses 6 hours apart.

Second, the sulfated oligosaccharides were tested for their ability to inhibit a mouse model of chronic asthma. This model is characterised by a massive influx of eosinophils into the lungs of mice which is induced by aeroallergen challenge (41). Such an inflammatory response is characteristic of chronic asthma in humans. When administered via miniosmotic pumps maltohexaose sulfate and mannopentaose sulfate significantly inhibited eosinophil accumulation in mouse lungs (Table 5). Maltohexaose sulfate also exhibited some anti-inflammatory activity when administered as an aerosol (40 mg/ml solution).

Third, both mannopentaose sulfate and sulfated mannopentaose phosphate significantly inhibited EAE in a rat model of the disease (Table 6). In fact, some animals treated with the sulfated oligosaccharides failed to develop disease symptoms. These data are consistent with earlier studies showing that sulfated polysaccharides which inhibit heparanase activity can reduce the severity of EAE (43).

Finally, mannopentaose phosphate was examined for its ability to inhibit an inflammatory bowel disease model in mice. This model, which is induced by dextran sulfate in the drinking water, induces a colitis which resembles ulcerative colitis and, to a lesser extent, Chron's disease. It was found that at 20 mg/kg/day sulfated mannopentaose phosphate caused a marked attenuation of acute colitis and also prevented loss of body weight caused by the disease (Table 7). The controls in this experiment received the sulfated oligosaccharide injections but not the dextran sulfate in heir drinking water.

TABLE 1

INHIBITION OF HUMAN ANGIOGENESIS, HEPARANASE ACTIVITY AND METASTASIS BY SULFATED FORMS OF DIFFERENT NATURALLY OCCURRING OLIGOSACCHARIDES

| Compound | Number of Saccharide Units | Anticoagulant Activity[a] (%) | 50% Inhibitory Concn ($\mu$g/ml) | | Metastasis (% Control)[b] |
|---|---|---|---|---|---|
| | | | Angiogenesis | Heparanase | |
| Heparin | Approx. 60 | 100 | >2000 | 1 | 20±3 |
| Mannopentaose phosphate SO$_4$[c] | 5 | 0.2 | 2 | 2 | 31 ± 3 |
| Raffinose SO$_4$ | 3 | 1.6 | 200 | 50 | 48 ± 9 |
| Stachyose SO$_4$ | 4 | 3.2 | 2000 | 12 | 36±4 |
| Maltose SO$_4$ | 2 | 0 | 2000 | >1000 | 99 ± 9 |
| Maltotetraose SO$_4$ | 4 | 0.8 | 20 | 10 | 72 ± 9 |
| Maltohexaose SO$_4$ | 6 | 1.6 | 2 | 1.5 | 24±7 |
| Cyclohexaamylose SO$_4$ | 6 | 0.4 | 200 | 8 | 107 ± 7 |
| Cycloheptaamylose SO$_4$ | 7 | 0.8 | 200 | 7 | 81 ± 14 |
| Cyclooctaamylose SO$_4$ | 8 | 1.6 | 200 | 5 | 36±6 |

TABLE 1-continued

INHIBITION OF HUMAN ANGIOGENESIS, HEPARANASE ACTIVITY AND METASTASIS BY SULFATED FORMS OF DIFFERENT NATURALLY OCCURRING OLIGOSACCHARIDES

| Compound | Number of Saccharide Units | Anticoagulant Activity[a] (%) | 50% Inhibitory Concn ($\mu$g/ml) Angiogenesis | Heparanase | Metastasis (% Control)[b] |
|---|---|---|---|---|---|
| Chondroitin tetra SO$_4$ | 4 | 0 | 2000 | >30 | ND |
| Chondroitin hexa SO$_4$ | 6 | 0.2 | 2000 | 45 | ND |
| Chondroitin octa SO$_4$ | 8 | ND | 1000 | ND | ND |
| Suramin | — | 0.1 | 50 | 8 | 74 ± 8 | a Anticoagulant activity as percentage of heparin activity (100%).
b Percentage control metastasis ± standard error of mean (n = 4) in lungs of rats receiving 13762 MAT cells i.v. and 2 mg/rat of each oligosaccharide at time of tumour cell injection. Underlined values represent compounds with the greatest anti-metastatic effect.
c Mannopentaose phosphate isolated from the yeast *Pichia holstii*
ND Not determined.

TABLE 2

INHIBITION OF HEPARANASE ACTIVITY AND GROWTH FACTOR BINDING TO HEPARAN SULFATES BY SULFATED MANNOPENTAOSE PHOSPHATE AND THE MALTOSE SERIES OF SULFATED OLIGOSACCHARIDES

| Sulfated Oligosaccharide | Sulfation[a] | % Sulfation | Anticoagulant Activity (%)[b] | IC50 ($\mu$g/ml)[c] Heparanase | bFGF | aFGF |
|---|---|---|---|---|---|---|
| Maltose | 6/8 | 75 | 0.2 | >100 | >200 | 134 |
| Maltotriose | 10/11 | 91 | 0.8 | 100 | 145 | 58.7 |
| Maltotetraose | 11/14 | 79 | 1.6 | 25 | 65 | 31.5 |
| Maltopentaose | 15/17 | 88 | 3.2 | 4 | 37.5 | 27 |
| Maltohexaose | 18/20 | 90 | 2 | 5 | 31.3 | 27 |
| Maltoheptaose | 18/23 | 78 | 3.9 | 3 | 10 | 27 |
| Mannopentaose phosphate[d] | 10/16 | 63 | 0.2 | 5 | 25 | 22 |
| Maltohexaose | 3/20 | 15 | 0 | >100 | 187 | >200 |
| Maltohexaose | 9/20 | 45 | 0.8 | 50 | 45.6 | 79 |
| Maltohexaose | 14/20 | 70 | 0.4 | 20 | 12.5 | 12.5 |
| Maltohexaose | 17/20 | 85 | 1.7 | 6 | 5.4 | 10.4 |
| Maltohexaose | 18/20 | 90 | 2 | 6 | 5.4 | 18.8 |
| Maltohexaose | 20/20 | 100 | 3.3 | 5 | 5.4 | 19.7 | a Actual number of sulfate groups attached/theoretical maximum number of sulfate groups which can be coupled to each molecule.
b Anticoagulantactivity as a percentage of heparin activity (100%).
c Concentration of compound required to inhibit by 50% human platelet heparanase activity, or binding of mouse 3T3 cells to immobilised aFGF/bFGF. In the case of the heparanase assay, the IC50 for heparin was 2 $\mu$g/ml.
d Mannopentaose phosphate isolated from the yeast *Pichia holstii*.
ND = not determined.

TABLE 3

INHIBITION OF HEPARANASE ACTIVITY, GROWTH FACTOR BINDING TO HEPARAN SULFATES BY SULFATED FORMS OF DIFFERENT SYNTHETIC OLIGOSACCHARIDES

| Sulfated Oligosaccharide | Sulfation[a] | % Sulfation | Anticoagulant Activity (%)[b] | IC50 ($\mu$g/ml)[c] Heparanase | bFGF | aFGF |
|---|---|---|---|---|---|---|
| Mannotriose | 7/11 | 64 | 0.3 | 25 | ND | ND |
| Mannotetraose | 10/14 | 71 | 0.4 | 6 | 20 | 5 |
| Mannopentaose | 12/17 | 71 | 0.4 | 4 | 15 | 5 |
| Mannohexaose | 11/20 | 55 | 0.8 | 3 | 11 | 5 |
| Galactotriose | 6.6/11 | 60 | 0.7 | 4 | 25 | ND |
| Galactotetraose | 8.3/14 | 59 | 1.0 | 3.5 | 9 | ND |
| Galactohexaose | 14.5/17 | 72.5 | 0.7 | 3.5 | 11 | ND |
| Glucotriose | ND | ND | 0.1 | 30 | 47 | ND |
| Glucohexaose | 13.4/20 | 67 | 0.4 | 3.5 | 15 | ND |

TABLE 3-continued

INHIBITION OF HEPARANASE ACTIVITY, GROWTH FACTOR BINDING TO HEPARAN SULFATES BY SULFATED FORMS OF DIFFERENT SYNTHETIC OLIGOSACCHARIDES

| Sulfated Oligosaccharide | Sulfation[a] | % Sulfation | Anticoagulant Activity (%)[b] | IC50 ($\mu$g/ml)[c] | | |
|---|---|---|---|---|---|---|
| | | | | Heparanase | bFGF | aFGF | a Actual number of sulfate groups attached/theoretical maximum number of sulfate groups which can be coupled to each molecule.
b Anticoagulant activity as a percentage of heparin activity (100%).
c Concentration of compound required to inhibit by 50% human platelet heparanase activity, or binding of mouse 3T3 cells to immobilised aFGF/bFGF. In the case of the heparanase assay, the IC50 for heparin was 2 $\mu$g/ml.
ND = Not determined.

TABLE 4

EFFECT OF SULFATED OLIGOSACCHARIDES ON AIR POUCH INFLAMMATION[a]

| Treatment | Dose | Leukocyte Infiltrate in Air Pouch[b] (% Control) | |
|---|---|---|---|
| | | Expt 1 | Expt 2 |
| Maltohexaose SO$_4$ | 50 mg/kg | 76 ± 7 | 44 ± 12 |
| Mannopentaose SO4 | 50 mg/kg | 57 ± 7 | 16 ± 2 |
| Mannopentaose phosphate SO4 (*P. holstii*) | 50 mg/kg | ND | 51 ± 9 |
| Prednisolone | 25 mg/kg | 56 ± 14 | 44 ± 3 | a Air pouch inflammation induced by thioglycollate injection and leucocyte influx assessed 17 hr later. Drug treatments were injected subcut. at the same time as the thioglycollate for Expt 1. In Expt 2., the sulfated oligosaccharides were injected subcut. 0 hr and 7 hr after thioglycollate injection.
b Data presented as percent control leukocyte number in an air pouch infiltrates ± standard error of mean. Controls were injected with thioglycollate but received no drug treatment, only a saline injection. The background leukocyte infiltrate in air pouches which were injected with saline alone was 9 ± 2% of that observed following thioglycollate injection.
ND = not determined.

TABLE 5

EFFECT OF SULFATED OLIGOSACCHARIDES ON OVALBUMIN (OVA) INDUCED EOSINOPHIL ACCUMULTION IN MOUSE LUNGS[a]

| Sulfated Oligosaccharide | Route | Dose | Eosinophils/ml BALF (% Control)[b] |
|---|---|---|---|
| Maltohexaose | Pump, i.p. | 50 mg/kg/day | 57 ± 2 |
| Maltohexaose | Pump, i.p. | 115 mg/kg/day | 9 ± 7 |
| Maltohexaose | Aerosol | 10 mg/ml[c] | 98 ± 24 |
| Maltohexaose | Aerosol | 40 mg/ml[c] | 63 ± 23 |
| Mannopentaose | Pump, i.p. | 50 mg/kg/day | 63 ± 12 | a Mice sensitised to OVA and then a lung eosinophil influx induced by aerosol administration of OVA. Sulfated oligosaccharides administered either i.p. with miniosmotic pumps or via the lungs as an aerosol.
b Data expressed as percent control eosinophil number in bronchoalveolar lavage fluid (BALF) ± standard error, controls being animals which were OVA challenged and received saline either via miniosmotic pumps or via the lungs as an aerosol.
c Concentration of sulfated oligosaccharide in the aerosol solution.

TABLE 6

EFFECT OF SULFATED OLIGOSACCHARIDES ON ADOPTIVELY TRANSFERRED EXPERIMENTAL AUTOIMMUNE ENCEPHALOMYELITIS (EAE)[a]

| Sulfated Oligosaccharide[b] | No. with EAE/Total | Mean Day Onset[c] | Disease Severity (% Control)[d] |
|---|---|---|---|
| Control | 6/6 | 5.5 ± 0.2 | 100 ± 11 |
| Mannopentaose | 3/5 | 5.3 ± 0.3 | 31.5 ± 15.1 |
| Mannopentaose phosphate (*P. holstii*) | 4/5 | 5.3 ± 0.3 | 47.9 ± 16.4 | a EAE induced in Lewis rats with 30 × 10$^6$ ConA activated EAE effector cells.
b Sulfated oligosaccharides, administered via subcut. miniosmotic pumps inserted at time of cell transfer, delivered a dose of 70 mg/kg/day.
c Mean day of onset of EAE in animals which developed disease.
d Disease severity represents cumulative clinical score of animals.

TABLE 7

EFFECT OF SULFATED MANNOPENTAOSE PHOSPHATE ON INFLAMMATORY BOWEL DISEASE IN MICE[a]

| | Untreated[c] | | Treated[c] | |
|---|---|---|---|---|
| Day[b] | Mean Disease Scored | Body Weight (gm) | Mean Disease Score[d] | Body Weight (gm) |
| 0 | 0 | 23.1 | 0 | 22.1 |
| 1 | 0 | 23.2 | 0 | 22.1 |
| 2 | 0 | 23.6 | 0 | 22.6 |
| 3 | 0 | 23.5 | 0 | 22.5 |
| 4 | 0 | 23.3 | 0 | 21.9 |
| 5 | 0 | 23.4 | 0 | 21.9 |
| 6 | 0.47 | 23.3 | 0.07 | 22.4 |
| 7 | 1.40 | 22.7 | 0.40 | 22.4 |
| 8 | 2.47 | 22.1 | 0.40 | 22.3 |
| 9 | 2.87 | 21.4 | 0.67 | 22.2 |
| 10 | 2.00 | 20.7 | 0.93 | 22.1 | a Inflammatory bowel disease induced by the administration of dextran sulfate in the drinking water.
b Days after initiation of dextran sulfate administration.
c Untreated animals received thrice daily injections of vehicle whereas treated animals received thrice daily injections of sulfated mannopentaose phosphate at a dose of 20 mg/kg/day.
d Mean disease score represents the sum of both diarrhoea and rectal bleeding scores for the animals at each time point.

REFERENCES

1. Dietrich, C. P., Nader, H. B. and Strauss, A. J. (1983). *Biochem. Biophys. Res. Comm.* 111 865–871.
2. Kjellen, L and Lindahl, U. (1991). *Annu. Rev. Biochem.* 60, 443–475.
3. David, G. (1993). *FASEB J.* 7, 1023–1030.
4. Esko, J. D. (1991). *Curr. Opin. Cell Biol.* 3, 805–816.
5. Cole, G. J. and Akeson, R. (1989). *Neuron* 2, 1157–1165.
6. Coombe, D. R., Watt, S. M. and Parish C. R. *Blood* 84, 739–752.
7. Yayon, A., Klagsbrun, M., Esko, J. D., Leder, P. and Ornitz, D. M. (1991). *Cell* 64, 841–848.
8. Rapraeger, A. C., Krufka, A. and Olwin, B. B. (1991). *Science* 252, 1705–1708.
9. Gitay-Goren, H., Soker, S., Vlodavsky, I. and Neufeld, G. (1992). *J. Biol. Chem.* 267, 6093–6098.
10. Yurchenco, P. D. and Schittny, J. C. (1990). *FASEB J.* 4, 1577–1590.
11. Stetler, S. W., Aznavoorian, S. and Liotta, L. A. (1993). *Annu. Rev. Cell Biol.* 9, 541–573.
12. Eldor, A., Bar-Ner, N., Fuks, Z. and Vlodavsky, I. (1987). *Semin. Thromb. Hemost.* 13, 475–488.
13. Nakajima, M., Irimura, T. and Nicolson, G. L. (1988). *J. Cell Biochem.* 36, 157–167.

14. Turnbull, J. E., Fernig, D. G., Ke, Y., Wilkinson, M. C. and Gallagher, J. T. (1992). *J. Biol. Chem.* 267, 10337–10341.
15. Mach, H., Volkin, D., Burke, C. J., Middaugh, C. R., Linhardt, R. J., Fromm, J. R. and Loganathan, D. (1993). *Biochemistry* 32, 5480–5489.
16. Nurcombe, V., Ford, M. D., Windschut, J. A. and Bartlett, P. F. (1993). *Science* 260, 103–106.
17. Spivak-Kroizman, T., Lemmon, M. A., Dikic, I., Ladbury, J. E., Pinchasi, D., Huang, J., Jaye, M., Crumley, G., Schlessinger, J. and Lax, I. *Cell* 79, 1015–1024.
18. Folkman, J. and Brem, H. (1992). Angiogenesis and inflammation. In: "Inflammation. Basic Principles and Clinical Correlates". Eds Gallin, J. I. Goldstein, I. M. and Snyderman, R. S., Raven Press, New York.
19. Folkman, J. (1991). Tumour angiogenesis. In "Cancer Medicine". Ed Holland, J. F., Lea & Febiger, Philadelphia.
20. Folkman, J. and Klagsbrun, M. (1987). *Science* 235, 442–447.
21. Ratner, S. (1992). *Invasion Metastasis* 12, 82–100.
22. Mora, P. T. and Wood, D., *J. Amer. Chem. Soc.* 80, 693.
23. O'Colla, P. S. and Lee E. E., (1964). *J. Chem. Soc.* 2351–2354.
24. Evans, W. L., Reynolds, D. D. and Talley, E. A., (1951). *Adv. Carbohyd. Chem.* 6, 27.
25. Goldstein, I. J. and Hullar, T. L., (1966). *Adv. Carbohyd. Chem.* 21, 431–512.
26. Haq. S. and Whelan, W. J., (1956). *J. Chem. Soc.* 4543.
27. Okada, M., Sumitomo, H., Sumi, K and Sugimoto, T., (1984). *J. Amer. Chem. Soc.* 17, 2451–2453.
28. Okada, M., Sumitomo, H., Hirasawa, T., Ihara, K. and Tada, Y., (1986). *Polym. J.*, (Tokyo), 18, 601–611.
29. O'Colla, P. S. and McGrath, D., (1962). *Chem. Ind.,* 178–179.
30. McGrath, D., Lee, E. E. and O'Colla, P. S., (1969). *Carbohydrate Res.,* 11, 453–460.
31. Reynolds, D. D., and Evans, W. L., *J. Amer. Chem. Soc.* (1947), 69, 66.
32. Glaser, J. H. and Conrad, H. E. (1979). *J. Biol. Chem.* 254, 6588–6597.
33. Anderson, R. F., Cadmus, M. C., Benedict, R. G. and Slodki, M. E. (1960). *Arch. Biochem. Biophys.* 89, 289–292.
34. Bretthauer, R. K., Kaczorowski, G. J. and Weise, M. J. (1973). *Biochemisrty* 12, 1251–1256.
35. Parish, C. R., Coombe, D. R., Jakobsen, K. B., Bennett, F. A. and Underwood, P. A. (1987). *Int. J. Cancer* 40, 511–518.
36. Guo, Y. and Conrad, H. E. (1989). *Anal. Biochem.* 176, 96–104.
37. Rylatt, D. B., Sia, D. Y., Mundy, J. R. and Parish, C. R. (1981). *Eur. J. Biochem.* 119, 641–646.
38. Brown, K. J., Hendry, I. A. and Parish, C. R. (1995). *Exp. Cell Res.* 217, 132–139.
39. Brown, K. J. and Parish, C. R. (1994). *Biochemistry* 33, 13918–13927.
40. Forrest, M. J., Brooks, P. M., Takagi, T. and Kowanko, I. (1988). In: "CRC Handbook of Animal Models for the Rheumatic Diseases". Eds. Greenwald, R. A. and Diamond, K. S., CRC Press, Boca Raton, Vol. 1, p.125.
41. Foster, P. S., Hogan, S. P., Ramsay, A. J., Matthaei, K. I. and Young,. (1996). *J. Exp. Med.* 183, 195–201.
42. Lelievre, S and Larsen, A. K. (1994). *Cancer Res.* 54, 3993–3997.
43. Willenborg, D. O. and Parish, C. R. (1988). *J. Immunol.* 140, 3401–3405.
44. Bartlett, M. R., Cowden, W. B. and Parish, C. R. (1995). *J. Leuk. Biol.* 57, 207–213.

What is claimed is:

1. A sulfated oligosaccharide, wherein the oligosaccharide has the formula I:

$$R_1-(R_x)_n-R_2 \qquad (I)$$

wherein $R_1$ and $R_2$ and each $R_x$ represents a hexose monosaccharide unit, all of which may be the same or different, adjacent hexose monosaccharide units being linked by at least one bond selected from the group consisting of 1→2, 1→3, 1→4 and 1→6 glycosidic bonds, wherein at least 55% of the available hydroxyl groups on the hexose monosaccharide units are O-sulfated, and n is an integer of from 1 to 6; with the proviso that the oligosaccharide is not a compound comprising 1→4 linked glucose residues or a compound comprising a 1→2 linked fructose.

2. A sulfated oligosaccharide according to claim 1 wherein n is from 1 to 4.

3. A sulfated oligosaccharide according to claim 1, wherein the monosaccharide units are hexoses selected from the group consisting of mannose, altrose, allose, talose, galactose, idose and gulose.

4. A sulfated oligosaccharide according to claim 1, wherein the oligosaccharide has the formula II:

$$R_y-(R_y)_n-R_y \qquad (II)$$

wherein each $R_y$ group is the same and each represents a hexose monosaccharide unit, adjacent hexose monosaccharide units being linked by at least one bond selected from the group consisting of 1–3, 1→4 and 1→6 glycosidic bonds; and n is an integer of from 1 to 6; with the proviso that the oligosaccharide is not a compound comprising 1→4 linked glucose residues.

5. A sulfated oligosaccharide according to claim 4, wherein n is from 1 to 4.

6. A sulfated oligosaccharide according to claim 4, wherein $R_y$ represents a monosaccharide unit which is a hexose selected from the group consisting of mannose, altrose, allose, talose, galactose, idose and gulose.

7. A sulfated oligosaccharide according to claim 6, wherein $R_y$ represents mannose or galactose.

8. A sulfated oligosaccharide according to claim 1, wherein the oligosaccharide is a naturally occurring oligosaccharide.

9. A sulfated oligosaccharide according to claim 1, wherein the oligosaccharide is derived from a naturally occurring polysaccharide.

10. A sulfated oligosaccharide according to claim 1, wherein the oligosaccharide is derived from chondroitin or the exopolysaccharide produced by the diploid yeast *Pichia holstii*.

11. A sulfated oligosaccharide according to claim 10, wherein the oligosaccharide is selected from chondroitin tetra-, hexa- and octosaccharides.

12. A sulfated oligosaccharide according to claim 11, wherein the oligosaccharide is mannopentaose phosphate from the yeast *Pichia holstii*.

13. A method for the anti-angiogenic treatment of a warm-blooded animal patient in need of such treatment, which comprises administration to the patient of an effective amount of a sulfated oligosaccharide selected from the group consisting of oligosaccharides having the formula I:

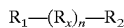

wherein $R_1$ and $R_2$ and each $R_x$ represents a hexose monosaccharide unit, all of which may be the same or different, adjacent hexose monosaccharide units being linked by at least one bond selected from the group consisting of 1→2, 1→3, 1→4 and 1→6 glycosidic bonds, wherein al least 55% of the available hydroxyl groups on the hexose monosaccharide units are O-sulfated, and n is an integer of from 1 to 6; with the proviso that the oligosaccharide is not a compound comprising 1→4 linked glucose residues or a compound comprising a 1→2 linked fructose.

14. A method according to claim 13, wherein the treatment comprises treatment of an angiogenesis-dependent disease selected from the group consisting of angiogenesis associated with the growth of solid tumours, proliferative retinopathies and rheumatoid arthritis.

15. A method according to claim 13, wherein the treatment comprises treatment of inflammatory diseases and conditions in which the heparanase-inhibitory activity of the sulfated oligosaccharide inhibits leukocyte infiltration.

16. A pharmaceutical or veterinary composition for anti-angiogenic treatment, which comprises a sulfated oligosaccharide selected from the group consisting of oligosaccharides having the formula 1:

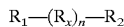

wherein $R_1$ and $R_2$ and each $R_x$ represents a hexose monosaccharide unit, all of which may be the same or different, adjacent hexose monosaccharide units being linked by at least one bond selected from the group consisting of 1→2, 1→3, 1→4 and 1→6 glycosidic bonds, wherein at least 55% of the available hydroxyl groups on the hexose monosaccharide units are O-sulfated, and n is an integer of from 1 to 6; with the proviso that the oligosaccharide is not a compound comprising 1→4 linked glucose residues or a compound comprising a 1→2 linked fructose, together with a pharmaceutically and veterinarily acceptable carrier or diluent therefor.

17. An oligosaccharide of the formula II:

$$R_y\text{—}(R_y)_n\text{—}R_y \qquad (II)$$

wherein each $R_y$ group is the same and each represents a hexose monosaccharide unit, adjacent hexose monosaccharide units being linked by at least one bond selected from the group consisting of 1→3, 1→4 and 1→6 glycosidic bonds; and n is an integer of from 1 to 6 ; with the proviso that the oligosaccharide is not a compound comprising 1→4 linked glucose residues.

18. An oligosaccharide according to claim 17, wherein n is from 1 to 4.

19. An oligosaccharide according to claim 17, wherein $R_y$ represents a monosaccharide unit which is a hexose selected from the group consisting of glucose, mannose, altrose, allose, talose, galactose, idose and gulose.

20. An oligosaccharide according to claim 19, wherein $R_y$ represents glucose, mannose or galactose.

21. An oligosaccharide according to claim 17 wherein $R_y$ is a fully O-acetylated monosaccharide, or wherein $R_y$ is a monosaccharide fully O-esterified with an acyl moiety other than acetyl.

22. A method for the anti-metastatic treatment of a warm-blooded animal patient in need of such treatment, which comprises administration to the patient of an effective amount of a sulfated oligosaccharide selected from the group consisting of oligosaccharides having the formula I:

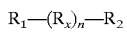

wherein $R_1$ and $R_2$ and each $R_x$ represents a hexose monosaccharide unit, all of which may be the same or different, adjacent hexose monosaccharide units being linked by at least one bond selected from the group consisting of 1→2, 1→3, 1→4 and 1→6 glycosidic bonds, wherein at least 55% of the available hydroxyl groups on the hexose monosaccharide units are O-sulfated, and n is an integer of from 1 to 6, with the proviso that the oligosaccharide is not a compound comprising 1→4 linked glucose residues or a compound comprising a 1→2 linked fructose.

23. A method for the anti-inflammatory treatment of a warm-blooded animal patient in need of such treatment, which comprises administration to the patient of an effective amount of a sulfated oligosaccharide selected from the group consisting of oligosaccharides having the formula I:

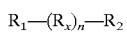

wherein $R_1$ and $R_2$ and each $R_x$ represents a hexose monosaccharide unit, all of which may be the same or different, adjacent hexose monosaccharide units being linked by at least one bond selected from the group consisting of 1→2, 1→3, 1→4 and 1→6 glycosidic bonds, wherein at least 55% of the available hydroxyl groups on the hexose monosaccharide units are O-sulfated, and n is an integer of from 1 to 6; with the proviso that the oligosaccharide is not a compound comprising 1→4 linked glucose residues or a compound comprising a 1→2 linked fructose.

24. A pharmaceutical or veterinary composition for anti-metastatic treatment, which comprises a sulfated oligosaccharide selected from the group consisting of oligosaccharides having the formula I:

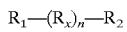

wherein $R_1$ and $R_2$ and each $R_x$ represents a hexose monosaccharide unit, all of which may be the same or different, adjacent hexose monosaccharide units being linked by at least one bond selected from the group consisting of 1→2, 1→3, 1→4 and 1→6 glycosidic bonds, wherein at least 55% of the available hydroxyl groups on the hexose monosaccharide units are O-sulfated, and n is an integer of from 1 to 6; with the proviso that the oligosaccharide is not a compound comprising 1→4 linked glucose residues or a compound comprising a 1→2 linked fructose, together with a pharmaceutically and veterinarily acceptable carrier or diluent therefor.

25. A pharmaceutical or veterinary composition for anti-inflammatory treatment, which comprises a sulfated oligosaccharide selected from the group consisting of oligosaccharides having the formula I:

$$R_1—(R_x)_n—R_2 \quad (I)$$

wherein $R_1$ and $R_2$ and each $R_x$ represents a hexose monosaccharide unit, all of which may be the same or different, adjacent hexose monosaccharide units being linked by at least one bond selected from the group consisting of 1→2, 1→3, 1→4 and 1→6 glycosidic bonds, wherein at least 55% of the available hydroxyl groups on the hexose monosaccharide units are O-sulfated, and n is an integer of from 1 to 6; with the proviso that the oligosaccharide is not a compound comprising 1→4 linked glucose residues or a compound comprising a 1→2 linked fructose, together with a pharmaceutically and veterinarily acceptable carrier or diluent therefor.

* * * * *

UNITED STATES PATENT AND TRADEMARK OFFICE
CERTIFICATE OF CORRECTION

PATENT NO. : 6,143,730
DATED : November 7, 2000
INVENTOR(S) : Christopher Richard Parish, William Butler Cowden It is certified that error appears in the above-identified patent and that said Letters Patent is hereby corrected as shown below:

Column 28, claim 4,
Line 34, change "1-3", to read -- 1→3 --.

Signed and Sealed this

Eleventh Day of December, 2001

Attest:

*Nicholas P. Godici*

NICHOLAS P. GODICI
*Attesting Officer*   *Acting Director of the United States Patent and Trademark Office*